US012727771B2

(12) United States Patent
Minor

(10) Patent No.: US 12,727,771 B2
(45) Date of Patent: Sep. 8, 2026

(54) WIRELESS HEART PRESSURE SENSOR SYSTEM AND METHOD

(71) Applicant: W. L. Gore & Associates, Inc., Newark, DE (US)

(72) Inventor: David J. Minor, Phoenix, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 877 days.

(21) Appl. No.: 17/909,493

(22) PCT Filed: Mar. 4, 2021

(86) PCT No.: PCT/US2021/020825
§ 371 (c)(1),
(2) Date: Sep. 6, 2022

(87) PCT Pub. No.: WO2021/178636
PCT Pub. Date: Sep. 10, 2021

(65) Prior Publication Data

US 2023/0165475 A1 Jun. 1, 2023

Related U.S. Application Data

(60) Provisional application No. 62/986,355, filed on Mar. 6, 2020.

(51) Int. Cl.
*A61B 5/0215* (2006.01)
*A61B 5/00* (2006.01)
(Continued)

(52) U.S. Cl.
CPC ............ *A61B 5/0215* (2013.01); *A61B 5/002* (2013.01); *A61B 5/0031* (2013.01); *A61B 5/318* (2021.01);
(Continued)

(58) Field of Classification Search
CPC ..... A61B 5/0215; A61B 5/002; A61B 5/0031; A61B 5/318; A61B 5/4836; A61B 5/6869;
(Continued)

(56) References Cited

U.S. PATENT DOCUMENTS 5,276,276 A 1/1994 Gunn
5,334,217 A 8/1994 Das
(Continued)

FOREIGN PATENT DOCUMENTS

CN 1819855 A 8/2006
CN 102271727 A 12/2011
(Continued)

OTHER PUBLICATIONS

Chuang et al., "Measurement of pulmonary artery diastolic pressure from a right ventricular pressure transducer in patients with heart failure", Journal of cardiac failure, vol. 2, No. 1, Mar. 1996, pp. 41-46.
(Continued)

*Primary Examiner* — Jennifer Robertson
*Assistant Examiner* — Jonathan Drew Moroneso

(57) ABSTRACT

Embodiments of the present disclosure relate to implantable cardiac sensors and associated diagnostic and treatment methods. In an exemplary embodiment, a medical system for determining a treatment regimen for a patient with a heart condition comprises a sensing device including a pressure sensor for monitoring and providing RVP information representative of right ventricle heart pressures. At least the pressure sensor is configured for implantation into a right ventricle of the patients heart. One or more processors are coupled to receive the RVP information and configured to determine a right atrial filling pressure based on the RVP information and a left atrial filling pressure based on the
(Continued)

RVP information. A display device displays the right atrial filling pressure and the left atrial filling pressure. In embodiments, the one or more processors determine the left and right atrial filling pressures using the right ventricular pressure as a surrogate.

28 Claims, 18 Drawing Sheets

(51) Int. Cl.

| | |
|---|---|
| ***A61B 5/02*** | (2006.01) |
| ***A61B 5/24*** | (2021.01) |
| ***A61B 5/318*** | (2021.01) |
| ***G16H 20/10*** | (2018.01) |

(52) U.S. Cl.

CPC .......... *A61B 5/4836* (2013.01); *A61B 5/6869* (2013.01); *A61B 5/6882* (2013.01); *A61B 5/7278* (2013.01); *A61B 5/7289* (2013.01); *G16H 20/10* (2018.01); *A61B 5/02* (2013.01); *A61B 5/24* (2021.01); *A61B 5/48* (2013.01); *A61B 5/68* (2013.01); *A61B 5/72* (2013.01); *A61B 2562/0247* (2013.01)

(58) Field of Classification Search

CPC ... A61B 5/6882; A61B 5/7278; A61B 5/7289; A61B 5/02; A61B 5/24; A61B 5/48; A61B 5/68; A61B 5/72; A61B 2562/0247; A61B 5/029; A61B 5/686; G16H 20/10; G16H 40/63; G16H 50/20

See application file for complete search history.

(56) References Cited

U.S. PATENT DOCUMENTS

| | | | | |
|---|---|---|---|---|
| 5,368,040 | A | 11/1994 | Carney | |
| 5,683,411 | A | 11/1997 | Kavteladze et al. | |
| 5,824,055 | A | 10/1998 | Spiridigliozzi et al. | |
| 5,944,738 | A | 8/1999 | Amplatz et al. | |
| 6,042,602 | A | 3/2000 | Wells | |
| 6,042,605 | A | 3/2000 | Martin et al. | |
| 6,077,291 | A | 6/2000 | Das | |
| 6,080,182 | A | 6/2000 | Shaw et al. | |
| 6,461,665 | B1 | 10/2002 | Scholander | |
| 6,500,204 | B1 | 12/2002 | Igaki | |
| 6,911,037 | B2 | 6/2005 | Gainor et al. | |
| 6,915,162 | B2 | 7/2005 | Noren et al. | |
| 6,926,670 | B2 | 8/2005 | Rich et al. | |
| 7,001,409 | B2 | 2/2006 | Amplatz | |
| 7,049,380 | B1 | 5/2006 | Chang et al. | |
| 7,128,073 | B1 | 10/2006 | van der Burg et al. | |
| 7,236,821 | B2 | 6/2007 | Cates et al. | |
| 7,462,675 | B2 | 12/2008 | Chang et al. | |
| 7,871,659 | B2 | 1/2011 | Cook et al. | |
| 7,887,562 | B2 | 2/2011 | Young et al. | |
| 7,901,702 | B2 | 3/2011 | Schwarz | |
| 8,021,331 | B2 | 9/2011 | Herweck et al. | |
| 8,043,360 | B2 | 10/2011 | Mcnamara et al. | |
| 8,048,440 | B2 | 11/2011 | Chang et al. | |
| 8,480,707 | B2 | 7/2013 | Pavcnik et al. | |
| 8,545,525 | B2 | 10/2013 | Surti et al. | |
| 8,696,693 | B2 | 4/2014 | Najafi et al. | |
| 8,715,300 | B2 | 5/2014 | Najafi et al. | |
| 8,728,103 | B2 | 5/2014 | Surti et al. | |
| 9,241,695 | B2 | 1/2016 | Peavey et al. | |
| 9,314,556 | B2 | 4/2016 | Tuseth | |
| 9,358,371 | B2 | 6/2016 | Mcnamara et al. | |
| 9,399,085 | B2 | 7/2016 | Cleek et al. | |
| 9,456,812 | B2 | 10/2016 | Finch et al. | |
| 9,545,300 | B2 | 1/2017 | Cully et al. | |
| 9,554,786 | B2 | 1/2017 | Carley et al. | |
| 9,629,715 | B2 | 4/2017 | Nitzan et al. | |
| 9,636,094 | B2 | 5/2017 | Aurilia et al. | |
| 9,649,481 | B2 | 5/2017 | Sadanand | |
| 9,681,948 | B2 | 6/2017 | Levi et al. | |
| 9,757,107 | B2 | 9/2017 | Mcnamara et al. | |
| 9,775,591 | B2 | 10/2017 | Delgado et al. | |
| 9,861,346 | B2 | 1/2018 | Callaghan | |
| 9,878,162 | B2 | 1/2018 | Mika et al. | |
| 9,949,728 | B2 | 4/2018 | Cahill | |
| 11,540,731 | B2 | 1/2023 | Minor et al. | |
| 2002/0077555 | A1 | 6/2002 | Schwartz | |
| 2002/0077556 | A1 | 6/2002 | Schwartz | |
| 2002/0169475 | A1 | 11/2002 | Gainor et al. | |
| 2002/0173742 | A1 | 11/2002 | Keren et al. | |
| 2003/0055344 | A1 | 3/2003 | Eigler et al. | |
| 2003/0139819 | A1 | 7/2003 | Beer et al. | |
| 2003/0170241 | A1 | 9/2003 | Aukrust et al. | |
| 2004/0049211 | A1 | 3/2004 | Tremulis et al. | |
| 2004/0063805 | A1 | 4/2004 | Pacetti et al. | |
| 2004/0073242 | A1 | 4/2004 | Chanduszko | |
| 2005/0038351 | A1 | 2/2005 | Starobin et al. | |
| 2005/0065545 | A1 | 3/2005 | Wallace | |
| 2005/0148925 | A1 | 7/2005 | Rottenberg et al. | |
| 2005/0288782 | A1 | 12/2005 | Moaddeb et al. | |
| 2006/0008500 | A1 | 1/2006 | Chavan et al. | |
| 2006/0079736 | A1 | 4/2006 | Chin et al. | |
| 2006/0116590 | A1 | 6/2006 | Fayram et al. | |
| 2006/0149330 | A1 | 7/2006 | Mann et al. | |
| 2006/0198866 | A1 | 9/2006 | Chang et al. | |
| 2006/0271116 | A1 | 11/2006 | Stahmann et al. | |
| 2007/0032734 | A1 | 2/2007 | Najafi et al. | |
| 2007/0118039 | A1 | 5/2007 | Bodecker et al. | |
| 2007/0118213 | A1 | 5/2007 | Loulmet | |
| 2007/0197921 | A1* | 8/2007 | Cohen | A61B 5/02116 600/485 |
| 2007/0244518 | A1 | 10/2007 | Callaghan | |
| 2007/0282430 | A1 | 12/2007 | Thommen et al. | |
| 2008/0064966 | A1 | 3/2008 | Brockway et al. | |
| 2008/0097227 | A1 | 4/2008 | Zdeblick et al. | |
| 2008/0221551 | A1 | 9/2008 | Goodson et al. | |
| 2008/0249562 | A1 | 10/2008 | Cahill | |
| 2008/0262518 | A1 | 10/2008 | Freudenthal | |
| 2008/0269551 | A1 | 10/2008 | Annest et al. | |
| 2008/0281212 | A1 | 11/2008 | Nunez et al. | |
| 2009/0024042 | A1 | 1/2009 | Nunez et al. | |
| 2009/0030331 | A1 | 1/2009 | Hochareon et al. | |
| 2009/0221923 | A1 | 9/2009 | Uemura et al. | |
| 2009/0240427 | A1 | 9/2009 | Siereveld et al. | |
| 2010/0049313 | A1 | 2/2010 | Alon et al. | |
| 2010/0056978 | A1 | 3/2010 | Machan et al. | |
| 2010/0069778 | A1 | 3/2010 | Bornzin et al. | |
| 2010/0094144 | A1* | 4/2010 | Doron | A61N 1/36564 600/509 |
| 2010/0094401 | A1 | 4/2010 | Kolbel et al. | |
| 2010/0114230 | A1* | 5/2010 | Audit | A61B 5/4836 607/18 |
| 2010/0150920 | A1 | 6/2010 | Glaser | |
| 2010/0241241 | A1 | 9/2010 | Mcknight et al. | |
| 2010/0262206 | A1 | 10/2010 | Zdeblick et al. | |
| 2011/0071623 | A1 | 3/2011 | Finch et al. | |
| 2011/0098767 | A1 | 4/2011 | Sugimachi et al. | |
| 2011/0153010 | A1 | 6/2011 | Hanna | |
| 2011/0208077 | A1 | 8/2011 | Soriano et al. | |
| 2011/0295183 | A1 | 12/2011 | Finch et al. | |
| 2011/0295366 | A1 | 12/2011 | Finch et al. | |
| 2011/0303229 | A1 | 12/2011 | Najafi et al. | |
| 2012/0136385 | A1 | 5/2012 | Cully | |
| 2012/0209345 | A1* | 8/2012 | Shkurovich | G16H 20/30 607/23 |
| 2012/0265296 | A1* | 10/2012 | McNamara | A61B 17/11 604/503 |
| 2013/0030521 | A1 | 1/2013 | Nitzan et al. | |
| 2013/0144379 | A1 | 6/2013 | Najafi et al. | |
| 2013/0165967 | A1 | 6/2013 | Amin et al. | |
| 2013/0281988 | A1 | 10/2013 | Magnin et al. | |
| 2014/0012368 | A1 | 1/2014 | Sugimoto et al. | |
| 2014/0107437 | A1 | 4/2014 | Pinsky | |
| 2014/0128795 | A1 | 5/2014 | Keren et al. | |
| 2014/0142617 | A1 | 5/2014 | Larsen et al. | |
| 2014/0200662 | A1 | 7/2014 | Eftel et al. | |

(56) References Cited

U.S. PATENT DOCUMENTS

2014/0207153 A1 7/2014 Najafi et al.
2014/0222040 A1 8/2014 Park et al.
2014/0228683 A1 8/2014 Aoki et al.
2014/0343670 A1 11/2014 Bakis et al.
2014/0371843 A1 12/2014 Wilson et al.
2015/0039084 A1 2/2015 Levi et al.
2015/0142049 A1 5/2015 Delgado et al.
2015/0313599 A1 11/2015 Johnson et al.
2016/0045165 A1 2/2016 Braido et al.
2016/0058452 A1 3/2016 Brenneman et al.
2016/0263299 A1 9/2016 Xu et al.
2017/0028194 A1 2/2017 Bonner et al.
2017/0042705 A1 2/2017 Cook et al.
2017/0105711 A1 4/2017 Masters
2017/0106176 A1 4/2017 Taft et al.
2017/0135817 A1 5/2017 Tylis et al.
2017/0172766 A1 6/2017 Vong et al.
2017/0196673 A1 7/2017 Cully et al.
2017/0281339 A1 10/2017 Levi et al.
2017/0319823 A1 11/2017 Yacoby et al.
2017/0358942 A1 12/2017 Pugh et al.
2018/0000580 A1 1/2018 Wallace et al.
2018/0008830 A1 1/2018 Kaiser
2018/0055629 A1 3/2018 Oba et al.
2018/0098772 A1 4/2018 Goldshtein et al.
2018/0126179 A1 5/2018 Haasl et al.
2018/0160917 A1 6/2018 Liu et al.
2018/0280667 A1 10/2018 Keren
2019/0130069 A1 5/2019 Li et al.
2019/0231510 A1 8/2019 Rafiee et al.
2019/0282178 A1 9/2019 Volosin et al.
2019/0374343 A1 12/2019 Lashinski et al.
2020/0038567 A1 2/2020 Siess et al.
2020/0069426 A1 3/2020 Conklin et al.
2020/0085378 A1 3/2020 Burnett et al.
2020/0179663 A1 6/2020 Mcdaniel et al.
2020/0196876 A1 6/2020 Minor et al.
2020/0196943 A1 6/2020 Minor et al.
2020/0196944 A1 6/2020 Minor et al.
2020/0197178 A1 6/2020 Vecchio
2021/0259839 A1 8/2021 Cole et al.
2021/0290214 A1 9/2021 Cole et al.
2021/0361238 A1* 11/2021 Bak-Boychuk ...... A61B 5/0215
2022/0218352 A1* 7/2022 O'Halloran ............ A61B 5/686
2022/0323012 A1* 10/2022 Pool ..................... A61B 5/6879
2023/0116796 A1 4/2023 Cole et al.
2024/0130624 A1 4/2024 Vecchio

FOREIGN PATENT DOCUMENTS

CN 104414692 A 3/2015
CN 105473107 A 4/2016
CN 107411848 A 12/2017
CN 107847751 A 3/2018
CN 108289737 A 7/2018
CN 108472142 A 8/2018
EP 1264572 A1 12/2002
EP 2020248 A1 2/2009
EP 2637576 A1 9/2013
GB 1355373 A 6/1974
GB 1506432 A 4/1978
GB 1509023 A 4/1978
JP 07-502918 A 3/1995
JP 09-500806 A 1/1997
JP 2001-519694 A 10/2001
JP 2003-061917 A 3/2003
JP 2003-519542 A 6/2003
JP 2005-528181 A 9/2005
JP 2006-528023 A 12/2006
JP 2007-527742 A 10/2007
JP 2008-296041 A 12/2008
JP 2008-545471 A 12/2008
JP 2009-517137 A 4/2009
JP 2010-505481 A 2/2010
JP 2012-525210 A 10/2012
JP 2013-517890 A 5/2013
JP 2014-151049 A 8/2014
JP 2016-538094 A 12/2016
JP 2017-536857 A 12/2017
KR 10-2011-0050315 A 5/2011
WO 93/13712 A1 7/1993
WO 98/42276 A1 10/1998
WO 01/51123 A1 7/2001
WO 2003/103476 A2 12/2003
WO 2004/091411 A2 10/2004
WO 2005/074367 A2 8/2005
WO 2005/110535 A1 11/2005
WO 2006/054343 A1 5/2006
WO 2007/062299 A2 5/2007
WO 2008/040555 A2 4/2008
WO 2009/137755 A2 11/2009
WO 2010/129089 A2 11/2010
WO 2011/093941 A2 8/2011
WO 2012/091809 A1 7/2012
WO 2014/150106 A1 9/2014
WO 2015/109027 A2 7/2015
WO 2017/118738 A1 7/2017
WO 2018/017900 A1 1/2018
WO 2018/154025 A1 8/2018
WO 2019/126721 A1 6/2019

OTHER PUBLICATIONS

Eigler et al., "Cardiac Unloading with an Implantable Interatrial Shunt in Heart Failure: Serial Observations in an Ovine Model of Ischemic Cardiomyopathy", Structural Heart, vol. 1, No. (1-2), 2017, pp. 40-48.
Feldman et al., "Transcatheter Interatrial Shunt Device for the Treatment of Heart Failure Rationale and Design of the Randomized Trial to Reduce Elevated Left Atrial Pressure in Heart Failure (Reduce LAP-HF I)", Circulation Heart failure, vol. 9, No. 7, 2016, pp. 1-10.
Gregg et al., "Interatrial Shunting for Heart Failure The V-Wave Shunt", Presentation at the Transcatheter Cardiovascular Therapeutics (TCT) Congress in Denver, Colorado, 2017, 18 pages.
International Preliminary Report on Patentability received for PCT Patent Application No. PCT/US2019/065610, mailed on Jun. 24, 2021, 9 pages.
International Preliminary Report on Patentability received for PCT Patent Application No. PCT/US2019/068275, mailed on Jul. 1, 2021, 11 pages.
International Preliminary Report on Patentability received for PCT Patent Application No. PCT/US2019/068277, mailed on Jul. 1, 2021, 7 pages.
International Preliminary Report on Patentability received for PCT Patent Application No. PCT/US2019/068280, mailed on Jul. 1, 2021, 7 pages.
International Preliminary Report on Patentability received for PCT Patent Application No. PCT/US2019/068282, mailed on Jul. 1, 2021, 9 pages.
International Preliminary Report on Patentability received for PCT Patent Application No. PCT/US2021/020825, mailed on Sep. 15, 2022, 11 pages.
International Search Report and Written Opinion received for PCT Patent Application No. PCT/US2019/042248, mailed on Oct. 23, 2019, 18 pages.
International Search Report and Written Opinion received for PCT Patent Application No. PCT/US2019/042252, mailed on Oct. 21, 2019, 18 pages.
International Search Report and Written Opinion received for PCT Patent Application No. PCT/US2019/065610, mailed on Mar. 26, 2020, 12 pages.
International Search Report and Written Opinion received for PCT Patent Application No. PCT/US2019/068275, mailed on Jun. 25, 2020, 16 pages.
International Search Report and Written Opinion received for PCT Patent Application No. PCT/US2019/068277, mailed on Mar. 25, 2020, 13 pages.

(56) References Cited

OTHER PUBLICATIONS

International Search Report and Written Opinion received for PCT Patent Application No. PCT/US2019/068280, mailed on Mar. 25, 2020, 12 pages.
International Search Report and Written Opinion received for PCT Patent Application No. PCT/US2019/068282, mailed on Mar. 25, 2020, 15 pages.
International Search Report and Written Opinion received for PCT Patent Application No. PCT/US2021/013411, mailed on May 6, 2021, 11 pages.
International Search Report and Written Opinion received for PCT Patent Application No. PCT/US21/20825, mailed on Jun. 25, 2021, 18 pages.
Ohlsson et al., "Monitoring of pulmonary arterial diastolic pressure through a right ventricular pressure transducer", Journal of cardiac failure, vol. 1, No. 2, Mar. 1995, pp. 161-168.
Rosa et al., "Transcatheter Implantable Devices to Monitoring of Elevated Left Atrial Pressures in Patients with Chronic Heart Failure", Translational Medicine, Università degli Studi di Salerno, vol. 17, No. 4, Jul. 2017, pp. 19-24.
Sondergaard et al., "Transcatheter treatment of heart failure with preserved or mildly reduced ejection fraction using a novel interatrial implant to lower left atrial pressure", European Journal of Heart Failure, vol. 16, 2014, pp. 796-801.
Wei, X., Liu, X., Rosenzweig, A. What do we know about the cardiac benefits of exercise? Trends in Cardiovascular Medicine; 25(6) : 537-539. Aug. 2015 (Year: 2015).
Kapur NK et al. Mechanical circulatory support devices for acute right ventricular failure. Circulation. 2017;136:314-326 (Year: 2017).

* cited by examiner

100

Medication administration reference table

| LA/RA Pressure Treatment Algorithm | RAP Trending Below Normal (101) | RAP Trending Normal (102) | RAP Trending Above Normal (103) |
|---|---|---|---|
| (104) LAP Trending Below Normal | Reduce Diuretics | Reduse Vasodilators | Reduce Vasodilators |
| (105) LAP Trending Normal | Reduce Diuretics | Hold Meds | Increase Diuretics |
| (106) LAP Trending Above Normal | Increase Vasodilators | Increase Vasodilators | Increase Diuretics |

FIG. 9

WIRELESS HEART PRESSURE SENSOR SYSTEM AND METHOD

CROSS-REFERENCE TO RELATED APPLICATION

This application is a national phase application of PCT Application No. PCT/US2021/020825, internationally filed on Mar. 4, 2021, which claims the benefit of Provisional Application No. 62/986,355, filed Mar. 6, 2020, which are incorporated herein by reference in their entireties for all purposes.

FIELD

This disclosure relates generally to systems and methods for sensing heart chamber pressures and related diagnostic and treatment methods. Disclosed embodiments include implantable wireless sensors and methods for obtaining left and right heart pressures.

BACKGROUND

During the past decade, the number of coronary deaths in the United States has steadily decreased thanks to advancements in medical science and treatment, but the relative number of heart failure deaths has increased, indicating that more people are living with a high risk of heart failure than ever before. Generally, heart failure occurs when the heart cannot supply enough blood to the body. As a result, lower volume output leads to a higher filling pressure in the left heart to help compensate for the lack of output. Lower volume output also causes lower organ perfusion, including a reduction in kidney or renal perfusion. Reduced kidney perfusion can result in a retention of excess fluid. An acute decompensation episode is when fluid levels rise and/or vascular blood distribution declines to a state that causes the patient to experience fatigue and dyspnea (trouble breathing), thus presenting to the hospital. If left untreated, this may result in serious complications and ultimately death.

It has been observed that heart failure primarily initiates as a result of left-side heart issues. In a normal healthy heart, oxygenated blood is first carried from the pulmonary veins, through the left atrium, into the left ventricle, and into the aorta, after which the blood is carried throughout the body. Thereafter, deoxygenated blood is carried from the two vena cava into the right atrium, through the right ventricle, and into the pulmonary arteries, which then carry the blood into the lungs for oxygenation. The pumping performance of the left ventricle can be affected by the thickening/thinning of the left ventricular wall or by the aortic/mitral valve damage, causing less blood to be pumped to the rest of the body.

There are at least two categories of heart failures: HFrEF (heart failure with reduced ejection fraction) and HFpEF (heart failure with preserved ejection fraction). In HFrEF, the left ventricle fills with enough blood, but cannot pump enough blood out due to poor contraction of the heart muscle. This is also called systolic heart failure. In HFpEF, the heart can pump blood out normally, but the left ventricle fills with less blood due to poor relaxation of the heart muscle creating less blood volume in the ventricle. This is also called diastolic heart failure. In either case, there generally is not enough blood being pumped to the body. Less commonly, biventricular failure can occur, which is when the left heart cannot pump enough blood out to the body and the right heart cannot pump enough blood to the lungs.

Pharmacological treatments are commonly employed to reduce heart pressure and prevent acute decompensation episodes. Remotely, the particular drug used is often determined by a trial and error approach using sign/symptoms such as weight gain, or by a singular intra-cardiac blood pressure measurement. Medications that are used today to reduce heart pressure and prevent acute decompensation episodes primarily include diuretics and vasodilators (nitrates, hydralazine, ace inhibitors, etc.) while other medications can be beta-blockers, inotropes, and more. Diuretics primarily target excess fluid buildup (fluid retention) and work by making the kidney release more sodium into the urine. The sodium then takes water with it from the bloodstream, thereby decreasing the amount of fluid flowing through the blood vessels and ultimately reducing intra-cardiac blood pressure. Loop diuretics, which are common in chronic heart failure, are also known to have a vasodilator effect on the venous vasculature, causing an increase in venous capacitance. Therefore, diuretics primarily help lower the preload on the heart by reducing blood volume from circulation.

Vasodilators are medications that open or dilate blood vessels, which can include nitrates, hydralazine, ace-inhibitors, and angiotensin receptor blockers, to name a few. As a result, blood flows more easily through the vessels, primarily arterial resistance vessels, and the heart does not need to pump as hard, thereby reducing intra-cardiac blood pressure. Nitrates, for example, are venous dilators at very low initial doses, but primarily increasingly affect arterial dilation in moderate to high doses (typical dosage of heart failure). Unlike diuretics, vasodilator therapy is primarily used to help reduce vascular resistance and afterload on the heart, which enhances stroke volume and cardiac output and leads to secondary decreases in left ventricular preload and venous pressures resulting in lower left sided filling pressure. Beta-blockers work to make the heart pump slower, i.e. induces lower heart rate, and with less force, thereby reducing intra-cardiac blood pressure. Inotropes work to increase the strength of ventricular contraction and therefore increase the heart rate. This medication may be used in severe cases where extremely poor perfusion exists and a ventricular assist device (VAD) or heart transplant is needed.

Remote pulmonary artery pressure monitoring and a corresponding medication treatment algorithm utilizing guideline medications has been proven to be effective in reducing hospitalizations due to heart failure. As shown in FIG. 1A, by monitoring the correct predictive biomarkers and performing the appropriate early interventions, the risk of hospitalization in a patient is significantly lowered. For example, in the earliest stages preceding a potential hospitalization event, measurement devices that measure an increase in the filling pressure of the heart can allow for timely treatment, resulting in a prevention of the pending hospitalization. After increased filing pressures occur, when the heart experiences pre-symptomatic congestion, the intrathoracic impedance changes. Later, other signs like a sudden weight gain, swelling in the feet and ankles, weakness or shortness of breath (dyspnea), and changes in the frequency of urination show that the body is retaining fluid. At these points, however, the congestion is typically at a later stage that is dangerously close to a decompensation episode. Therefore, it is best to treat the earliest indications because by the time later symptoms occur prior to a decompensation episode develop, it may already be too late as permanent damage may have already been done to the organs.

To understand and treat a patient's heart failure, the hospital performs many acute analyses using various means of measurements. These include noninvasive measurements as well as invasive ones so that the medical service providers can get a better understanding of the patient's disease. Noninvasive measurements include: echocardiogram, which is used to diagnose the disease, monitor blood flow, and visualize changes in physiology; weight gain, which determines changes in fluid retention; visual inspection of the jugular vein, which determines fluid retention status; blood pressure readings, which estimate the blood flow of the body; heart rate; electrocardiography (ECG); and oxygen saturation. Invasive measurements include: right heart catheterization and left heart catheterization.

Right heart catheterization, which is performed using Swan-Ganz catheterization, can measure the central venous pressure, right atrial pressure (RAP), right ventricular diastolic and systolic pressures, pulmonary arterial diastolic and systolic pressures, and pulmonary artery wedge pressure (PAWP). Also, this method can measure the oxygen status, temperature, and heart rate of the patient, as well as calculate the cardiac output, systemic vascular resistance, and pulmonary vascular resistance. The right heart catheterization is primarily used to check pressures, cardiac output, resistance, and fluid status in the heart. Left heart catheterization can measure the left atrial pressure as well as the left ventricular diastolic and systolic pressures. The right heart catheter can be left in a patient for a few days while the medical service providers attempt to reduce the patient's intracardiac blood filling pressure back to acceptable levels using medications. This is an effective practice in an acute setting. During the ESCAPE clinical trial, the use of pressure measurements was determined as a viable means to improve a patient's overall status in the acute setting, for example by targeting a RAP of ≤8 mm Hg and a PAWP of ≤15 mm Hg. However, it was not an ongoing solution, and therefore did not prevent hospitalizations because the pressures were assumed to change relatively shortly after leaving the hospital. Therefore, a right heart catheter is primarily used to guide therapy to reduce symptoms and pressure in the acute setting.

Current diagnostic approaches can be divided into two broad settings: acute and remote. The acute setting occurs when a patient is assessed at the hospital using various methods (invasive or noninvasive). The remote setting corresponds to patient physiological parameters taken remotely, outside the hospital.

In the acute setting, a right heart catheterization may be used to give the medical service providers information for selecting appropriate medications. Generally, a right heart catheterization is viewed as useful for separating effects of volume and vascular resistance (e.g., by observing both PAWP and right atrial pressures). Medical service providers will look at the absolute values and ratios to distinguish between the two issues, particularly in the left heart failure, such that they know when fluid is offloaded and are then able to determine the status of the blood distribution. In current practice, the acute setting typically allows for more accurate measurement of the heart's health because pressure readings from different locations within the heart are taken into consideration simultaneously.

FIG. 1B is illustrative of the implementation of a right heart catheterization. The measurement device 40 is attached to the end of a pulmonary artery catheter 18 which passes through the right atrium 1, the tricuspid valve 7, the right ventricle 2, through the pulmonary valve 58, and into the pulmonary artery 16 where the device 40 takes measurement of the blood pressure as deoxygenated blood is carried into the lung 22. Then, fresh air is carried into the lung 22 from the trachea 23 after which oxygenated blood is carried through the pulmonary vein 17, the left atrium 3, the mitral valve 6, the left ventricle 4, and the aortic valve 57. The catheter 18 also has a proximal injection port which injects cold saline bolus 20 into the right atrium, and a thermistor 21 located at a distal end of the catheter to measure the temperature of the blood in the pulmonary artery 16. This method of measurement is known as thermodilution, which measures the blood flow based on the premise that when the cold saline bolus is added to the circulating blood, the rate of blood flow is inversely proportional to the rate of change in blood temperature resulting from the cold saline bolus over time. This provides a measure of cardiac output.

Pulmonary artery wedge pressure and pulmonary artery diastolic pressure may be used as surrogate measurements for the pressure within the left atrium and the filling pressure of the left ventricle, which is a typical area of concern in heart failure. It has been shown that the pulmonary artery and left ventricular filling pressures correlate on most occasions except for certain comorbidities such as primary pulmonary arterial hypertension. Such pressures change because of circulating volume increase (e.g. fluid retention) or declining pumping efficiency of the left ventricle (e.g., thickening, dilation, or vasoconstriction of the peripheral resistance vessels).

Various attempts have been made to remotely monitor cardiac pressures in order to identify more effective pharmacological treatment programs. These systems seek to monitor increases in intracardiac pressures to provide an early predictor of an impending acute decompensation for a patient with prior history of heart failure (e.g., as a much more reliable indicator than other measurements such as weight gain, thoracic impedance, etc.) For example, the CardioMEMS™ heart failure monitoring system by Abbott resides in the pulmonary artery and seeks to effectively monitor pulmonary artery pressures as a surrogate for left atrial pressure. Other examples of remote monitoring systems include: Chronicle® by Medtronic and HeartPOD™ by Abbott/St. Jude. The CardioMEMS, Chronicle and HeartPOD devices are described generally in the De Rosa et al. paper entitled Transcatheter Implantable Devices To Monitoring Of Elevated Left Atrial Presses In Patients With Chronic Heart Failure, Universita degli Studi di Salerno, Translational Medicine, 2017, 17(4): 19-21 (ISSN 2239-9747).

With Chronicle®, the measurement device resides in the right ventricle and reports an estimated pulmonary artery diastolic pressure (ePAD) to a receiving device. It has been stated that the measurements showed a correlation between right ventricular diastolic pressure, right ventricular systolic pressure, and ePAD, with the increase in all these pressure readings acting as indicators of an impending hospitalization.

HeartPOD™ uses a lead-and-can design with delivery of a measurement device by septal puncture method, with the measurement device remaining in the atrial septum and measuring left atrial pressure.

Another example includes the Vectorious™ left atrial pressure (LAP) monitoring system by Vectorious Medical Technologies which uses a pressure sensor to measure the blood pressure within the left atrium.

Over the past several decades, the development of remote systems has focused on finding a reliable predictor of upcoming hospitalization events. Measuring left sided filling pressure and surrogates have shown to be the most reliable, predictive, and effective form of remote monitoring. However, these systems show less information than acute right heart catheterization, as such systems provide limited data for accurately detecting root causes of the rise in pressure. One effect of limited data, whether in the remote or acute setting, is that medical service providers are required to utilize trial and error medication techniques for patient treatment. This remote trial and error practice can result in potential unnecessary harm to the patient, including kidney damage, further heart failure disease progression, or undetected comorbidities. For this reason, physicians are careful with their titration increases (slow increases/decreases), use creatinine lab testing as a lagging metric to detect kidney damage due to over-diuresis, and are worried about arising comorbidities (such as undetected right heart failure), and bring the patient into the office for further analysis, which may include the need for a right heart catheterization in order to determine a safe and effective treatment change.

For example, a medical service provider may first try diuretics to reduce the monitored blood pressure, if they assume that the pressure increase is due to a fluid retention issue. If this does not work, they may increase the dosage of diuretics again. If this still does not work, the medical service provider may decide that the problem is not in the fluid retention, but vascular resistance, after which an attempt may be made to use medications such as vasodilators. Lab creatinine testing may further reveal that over-diuresis (hypovolemia) led to increased damage of the kidneys. In other words, treatment methods often rely heavily on an individual medical service provider's personal experiences and intuition, which not only vary from provider-to-provider and patient-to-patient but may also extend the time needed to reliably arrive at a correct diagnosis.

There remains need for improved devices, systems and methods for physiologic measurements and associated diagnostic and treatment regimens for patients at risk of heart failure.

SUMMARY

Disclosed herein are methods and medical devices, such as implantable measurement devices, for performing measurements in a heart.

One exemplary embodiment is a medical system for determining a treatment regimen for a patient with a condition. The medical system comprises a sensing device including a pressure sensor for monitoring and providing RVP information representative of right ventricle heart pressures over a period of time, wherein at least the pressure sensor is configured for implantation into a right ventricle of the patient's heart; one or more processors, coupled to receive the RVP information, configured to: determine a right atrial filling pressure based on the RVP information; and determine a left atrial filling pressure based on the RVP information; and optionally a display device to display the right atrial filling pressure and the left atrial filling pressure, wherein the condition is at least one selected from the group of: left heart failure, right heart failure, and primary pulmonary disorder.

Embodiments of the medical system may further comprise a memory unit configured to store the right atrial filling pressure, the left atrial filling pressure and the condition of the patient; and wherein the one or more processors are configured to determine, based on the right atrial filling pressure, the left atrial filling pressure and the condition of the patient, the treatment regimen for the patient. The one or more processors may be coupled to receive the RVP information from the sensing device by a wireless communication link.

The sensing device of the medical system may comprise a wireless transmitter to wirelessly transmit the RVP information; and the one or more processors may be coupled to receive the RVP information wirelessly transmitted by the sensing device. The sensing device may comprise a housing configured for attachment to a wall (optionally free wall, apex, septum or outflow tract) in the right ventricle of the heart. The sensing device may comprise an anchor for attaching the sensing device to the wall of the right ventricle of the heart, and wherein the anchor optionally includes one or more of a coiled spring or a barbed hook. The sensing device may be configured to be entirely located in the right ventricle. The sensing device may comprise an antenna to receive electromagnetic energy; a wireless transmitter; and wherein the sensing device may be configured to be energized by electromagnetic energy received by the antenna, and to transmit the RVP information by the wireless transmitter when energized. In embodiments, the sensing device does not transmit the RVP information until it is energized.

In embodiments, the one or more processors of the medical system are configured to determine the right atrial filling pressure using the RVP information as a surrogate for the for the right atrial filling pressure. In embodiments, the one or more processors are configured to determining the right atrial filling pressure based on heart pressure information consisting of the RVP information. In embodiments, the one or more processors are configured to determine the right atrial filling pressure based on the RVP information at end diastole (e.g., using right ventricle end diastolic pressure as a surrogate for the right atrial filling pressure). In embodiments, the one or more processors are configured to receive electrical information, optionally ECG information, representative of electrical activity of the heart; identify a time of end diastole of the heart based on the electrical information; and determine the right atrial filling pressure based on the RVP information at the identified time of end diastole of the heart. The one or more processors may be configured to determine the left atrial filling pressure using the RVP information as a surrogate for the left atrial filling pressure. The one or more processors may be configured to determine the left atrial filling pressure based on a slope, and optionally a maximum or peak of the slope, of the RVP information. The one or more processors may be configured to determine the left atrial filling pressure using the right ventricular pressure represented by the RVP information at a time corresponding to the maximum or peak slope of the RVP information as a surrogate for estimated pulmonary artery diastolic pressure, and using the estimated pulmonary artery diastolic pressure as a surrogate for the left atrial filling pressure. The one or more processors may be configured to determine the left atrial filling pressure based on heart pressure information consisting of the RVP information. In embodiments, the system is configured to determine the right atrial filling pressure without directly monitoring pressure in the right atrium, and to determine the left atrial filling pressure without directly monitoring pressure in the left atrium. The sensing device may be configured to provide the RVP information over one or more cycles of diastole and systole. The one or more processors may be remote from a patient's body including a heart associated with the RVP information in embodiments. In embodiments, the sensing device acquires the RVP information at a frequency greater than 100 Hz, and optionally greater than 200 Hz.

In embodiments of the medical system, to determine the treatment regimen of the patient, the one or more processors may be configured to compare the right atrial filling pressure to a baseline right atrial pressure; and compare the left atrial filling pressure to a baseline left atrial pressure. To determine the treatment regimen of the patient, the one or more processors may be configured to compare the right atrial filling pressure and the left atrial filling pressure. To determine the treatment regimen for the patient, the one or more processors may be configured to provide a notification to increase the dosage of the treatment regimen. To determine the treatment regimen for the patient, the one or more processors may be configured to provide a notification to decrease the dosage of the treatment regimen.

In embodiments of the medical system, the one or more processors are incorporated into an implantable medical device. The one or more processors may be incorporated into a device located external to the patient. To determine the treatment regimen of the patient, the one or more processors may be configured to provide a notification to increase at least one treatment selected from the following group of treatments: vasodilators, diuretics, pulmonary vasodilators, neurohormonal antagonists, beta blockers, and inotropes. To determine the treatment regimen of the patient, the one or more processors may be configured to provide a notification to decrease at least one treatment selected from the following group of treatments: vasodilators, diuretics pulmonary vasodilators, neurohormonal antagonists, beta blockers, and inotropes.

Another exemplary embodiment is a computer-implemented method for determining a treatment regimen for a patient with a condition. Embodiments of the method comprise operating a sensing device including a pressure sensor located in a right ventricle of the patient's heart to monitor pressure in the right ventricle and to transmit RVP information representative of the pressure in the right ventricle over a period of time, optionally including implanting the pressure sensor in the right ventricle; processing the RVP information by one or more processors to determine a right atrial filling pressure for the patient based on the RVP information and a left atrial filling pressure for the patient based on the RVP information; and optionally displaying on a display device the right atrial filling pressure and the left atrial filling pressure, wherein the condition is at least one selected from the group of: left heart failure, right heart failure, and primary pulmonary disorder. In embodiments, the method further comprises determining the treatment regimen for the patient based on the right atrial filling pressure, the left atrial filling pressure, and the condition of the patient.

In embodiments, determining the right atrial filling pressure may comprise using the RVP information as a surrogate for the for the right atrial filling pressure. Determining the right atrial filling pressure may comprise determining the right atrial filling pressure based on heart pressure information consisting of the RVP information. Determining the right atrial filling pressure may comprise determining the right atrial filling pressure based on the RVP information at end diastole (e.g., using right ventricle end diastolic pressure as a surrogate for the right atrial filling pressure).

Embodiments of the method further comprise receiving electrical information, optionally ECG information, representative of electrical activity of the heart; and identifying a time of end diastole of the heart based on the electrical information; and determining the right atrial filling pressure comprises determining the right atrial filling pressure based on the RVP information at the identified time of end diastole of the heart (e.g., using right ventricle end diastolic pressure as a surrogate for the right atrial filling pressure). Determining the left atrial filling pressure may comprise using the RVP information as a surrogate for the left atrial filling pressure. Determining the left atrial filling pressure may comprise determining the left atrial filling pressure based on a slope, and optionally a maximum or peak of the slope, of the RVP information. Determining the left atrial filling pressure may comprise using the right ventricular pressure represented by the RVP information at a time corresponding to the maximum or peak slope of the RVP information as a surrogate for estimated pulmonary artery diastolic pressure, and using the estimated pulmonary artery diastolic pressure as a surrogate for the left atrial filling pressure. Determining the left atrial filling pressure may comprise determining the left atrial filling pressure based on heart pressure information consisting of the RVP information. Operating the sensing device to monitor pressure includes acquiring the RVP information at a frequency greater than 100 Hz, and optionally greater than 200 Hz, in embodiments.

In embodiments of the method, receiving the RVP information comprises receiving the RVP information from a sensing device comprising a single pressure sensor in the right ventricle. Receiving the RVP information may comprise receiving the RVP information from a sensing device entirely located in the right ventricle. Determining the left atrial filling pressure may comprise determining the right atrial filling pressure and determining the left atrial filling pressure based on the RVP information received from the single pressure sensor. In embodiments, receiving the RVP information comprises wirelessly receiving the RVP information.

In embodiments of the method, determining the right atrial filling pressure comprises determining the right atrial filling pressure without directly monitoring pressure in the right atrium; and determining the left atrial filling pressure comprises determining the left atrial filling pressure without directly monitoring pressure in the left atrium. The method may further comprise energizing an implanted sensing device comprising a pressure sensor located in the right ventricle, and wherein the energized sensing device transmits the RVP information. In embodiments, the implanted sensing device does not transmit the RVP information until it is energized. Receiving the RVP information representative of a right ventricle heart pressure over a period of time may comprise receiving the RVP information representative of a right ventricle heart pressure over one or more cycles of diastole and systole. In embodiments, the one or more processors may be remote from a patient's body including a heart associated with the RVP information.

In embodiments of the method, determining the treatment regimen of the patient may comprise comparing the right atrial filling pressure to a baseline right atrial pressure; and comparing the left atrial filling pressure to a baseline left atrial pressure. Determining the treatment regimen of the patient may comprise comparing the right atrial filling pressure and the left atrial filling pressure. Determining the treatment regimen for the patient may comprise providing a notification to increase the dosage of the treatment regimen. Determining the treatment regimen for the patient may comprise providing a notification to decrease the dosage of the treatment regimen. Determining the treatment regimen of the patient may comprise providing a notification to increase at least one treatment selected from the following group of treatments: vasodilators, diuretics, pulmonary vasodilators, neurohormonal antagonists, beta blockers, and inotropes. Determining the treatment regimen of the patient may comprise providing a notification to decrease at least one treatment selected from the following group of treatments: vasodilators, diuretics, and pulmonary vasodilators, neurohormonal antagonists, beta blockers, and inotropes.

Yet other exemplary embodiments includes a monitoring system, comprising a receiver configured to receive RVP information associated with a right ventricle heart pressure over a period of time, wherein the RVP information is received from a sensing device including a pressure sensor located in the right ventricle of the heart; a memory unit configured to store the received RVP information; optionally a display device; and one or more processors configured to determine a right atrial filling pressure based on the RVP information and a left atrial filling pressure based on the RVP information; compare the right atrial filling pressure and the left atrial filling pressure; and output, to the display device, the comparison. In embodiments, the one or more processors are further configured to determine, based on the comparison, a treatment regimen for the patient. The receiver receives RVP information acquired at a frequency greater than 100 Hz, and optionally greater than 200 Hz, in embodiments.

In embodiments of the monitoring system the one or more processors may be configured to determine the right atrial filling pressure using the RVP information as a surrogate for the for the right atrial filling pressure. The one or more processors may be configured to determine the right atrial filling pressure based on heart pressure information consisting of the RVP information. The one or more processors may be configured to determine the right atrial filling pressure based on the RVP information at end diastole (e.g., using right ventricle end diastolic pressure as a surrogate for the right atrial filling pressure). The one or more processors may be configured to receive electrical information, optionally ECG information, representative of electrical activity of the heart; identify a time of end diastole of the heart based on the electrical information; and determine the right atrial filling pressure based on the RVP information at the identified time of end diastole of the heart.

In embodiments of the monitoring system, the one or more processors may be configured to determine the left atrial filling pressure using the RVP information as a surrogate for the left atrial filling pressure. The one or more processors may be configured to determine the left atrial filling pressure based on a slope, and optionally a maximum or peak of the slope, of the RVP information. The one or more processors may be configured to determine the left atrial filling pressure using the right ventricular pressure represented by the RVP information at a time corresponding to the maximum or peak slope of the RVP information as a surrogate for estimated pulmonary artery diastolic pressure, and to use the estimated pulmonary artery diastolic pressure as a surrogate for the left atrial filling pressure. In embodiments, the one or more processors are configured to determine the left atrial filling pressure based on heart pressure information consisting of the RVP information. The system may be configured to determine the right atrial filling pressure without direct information about monitored pressure in the right atrium, and to determine the left atrial filling pressure without direct information about monitored pressure in the left atrium.

In embodiments of the monitoring system, the treatment comprises at least treatment selected from the following group of treatments: diagnosis, medication titrations, advanced therapy, IV medications, lifestyle changes, intra-atrial shunts, valve repair/replace, ICDs, CRTs, and ablation. The medication titrations may comprise at least one titration selected from the following group of titrations: vasodilators, diuretics, pulmonary vasodilators, neurohormonal antagonists, beta blockers, and inotropes. The advanced therapy may comprise one or more selected from the group of: implanting a ventricular assist device (VAD), implanting a mechanical circulator support (MCS), a transplant, or both. The lifestyle changes may comprise at least one lifestyle change selected from the following group of lifestyle changes: a change in diet, increased activity, or both.

In embodiments of the monitoring system, the one or more processors are further configured to output the determined treatment to the display device. The one or more processors may be further configured to diagnose, based on the comparison, the patient. In embodiments, the monitoring system is a closed loop system where trend data of the measurements inform changes to an automated dispensing of a medicine. The medicine may be a diuretic, vasodilator, or both. In embodiments, the monitoring system is a closed loop system where trend data of the measurements inform changes to a ventricular assist device. The monitoring system may be used to determine RPM changes in a ventricular assist device.

In embodiments, the one or more processors may use machine learning to modify the treatment regimen. The processing device may be further configured to output to the display device one or more of the following: left atrial pressure, left atrial pressure averages, right atrial pressure, right atrial pressure averages, trend arrows of the measurements, line graphs over time of the measurements, waveforms of the measurements, and one or more medications of a patient associated with the measurements.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 9 illustrates a medication administration reference table using two sets of measurement data as implemented by the method in FIG. 8;

DETAILED DESCRIPTION

This disclosure is not meant to be read in a restrictive manner. For example, the terminology used in the application should be read broadly in the context of the meaning those in the field would attribute such terminology.

As the terms are used herein with respect to ranges of measurements "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Certain terminology is used herein for convenience only. For example, words such as "top", "bottom", "upper," "lower," "left," "right," "horizontal," "vertical," "upward," and "downward" merely describe the configuration shown in the figures or the orientation of a part in the installed position. Indeed, the referenced components may be oriented in any direction. Similarly, throughout this disclosure, where a process or method is shown or described, the method may be performed in any order or simultaneously, unless it is clear from the context that the method depends on certain actions being performed first.

Various embodiments are directed toward implantable medical devices such as device for performing physiologic measurements to obtain information regarding characteristics in the left and right sides of the heart. In certain instances, the various aspects of the present disclosure relate to methods and devices for performing pressure measurements. Additionally, the present disclosure also includes a medical treatment system for determining administration of medications to a patient based on the measurements performed.

Figure 1A:
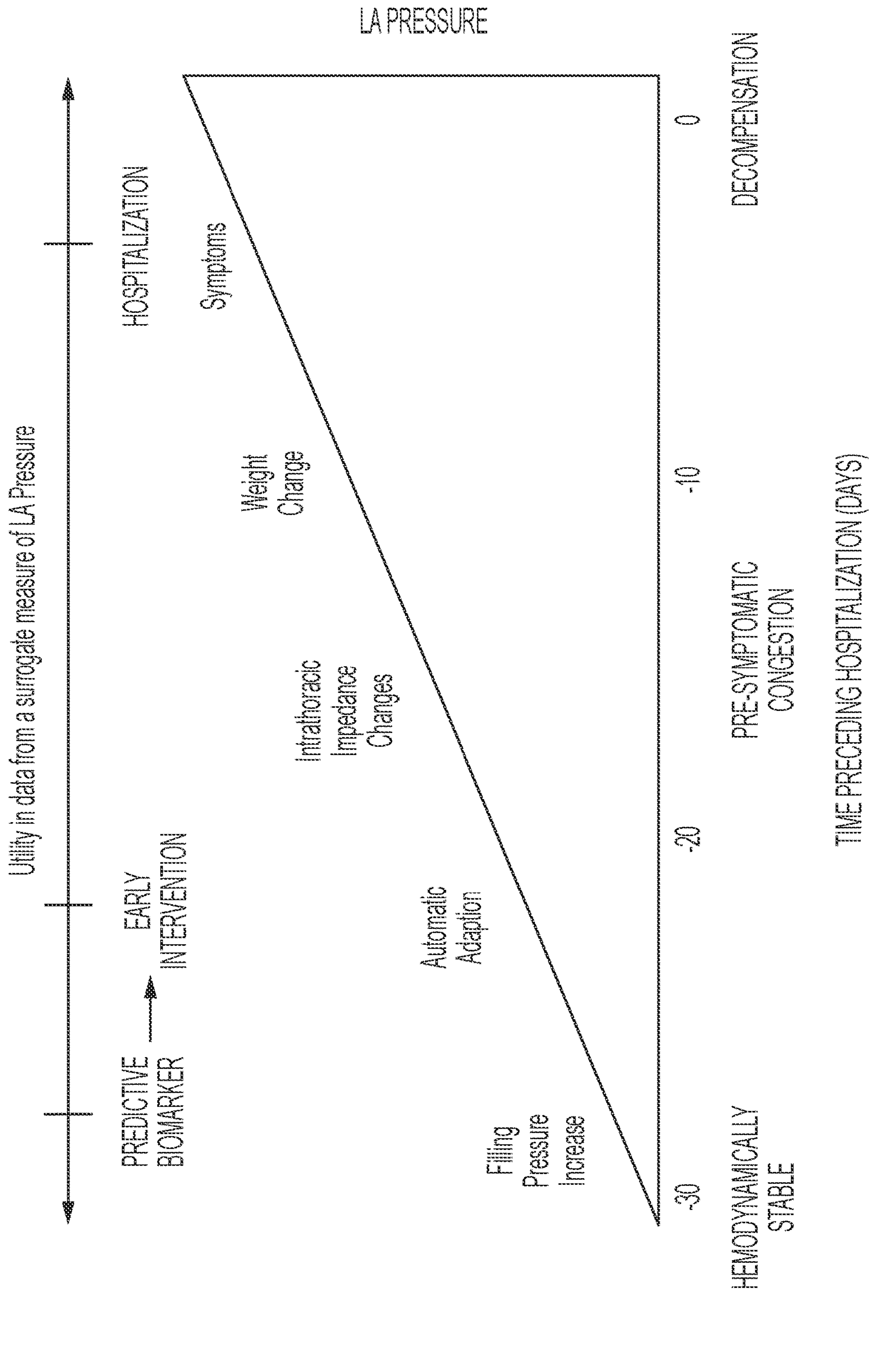
FIG. 1A is a graph showing the utility in data from a surrogate measurement of left atrial pressure in reducing hospitalizations due to heart failure.
Figure 1B:
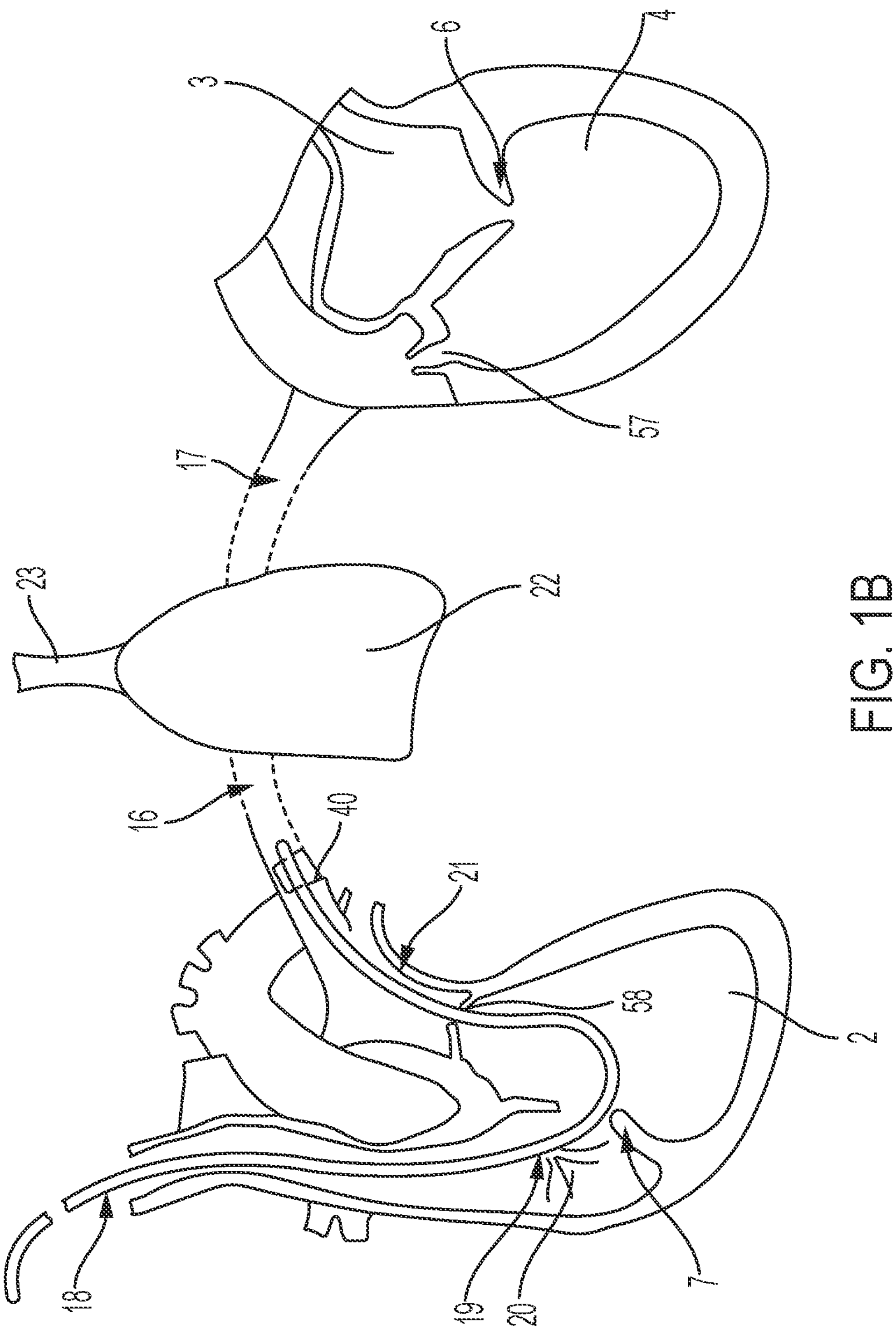
FIG. 1B is a schematic diagram of a heart and a lung of a patient using the prior-art measurement device (Swan Ganz right heart catheter) as discussed herein.
Figure 2:
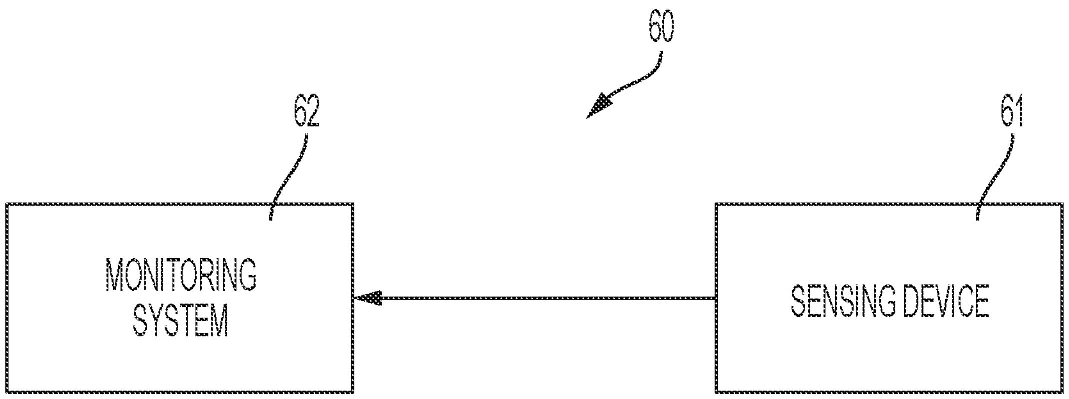
FIG. 2 is a diagrammatic illustration of a medical system according to some embodiments.
Figure 3:
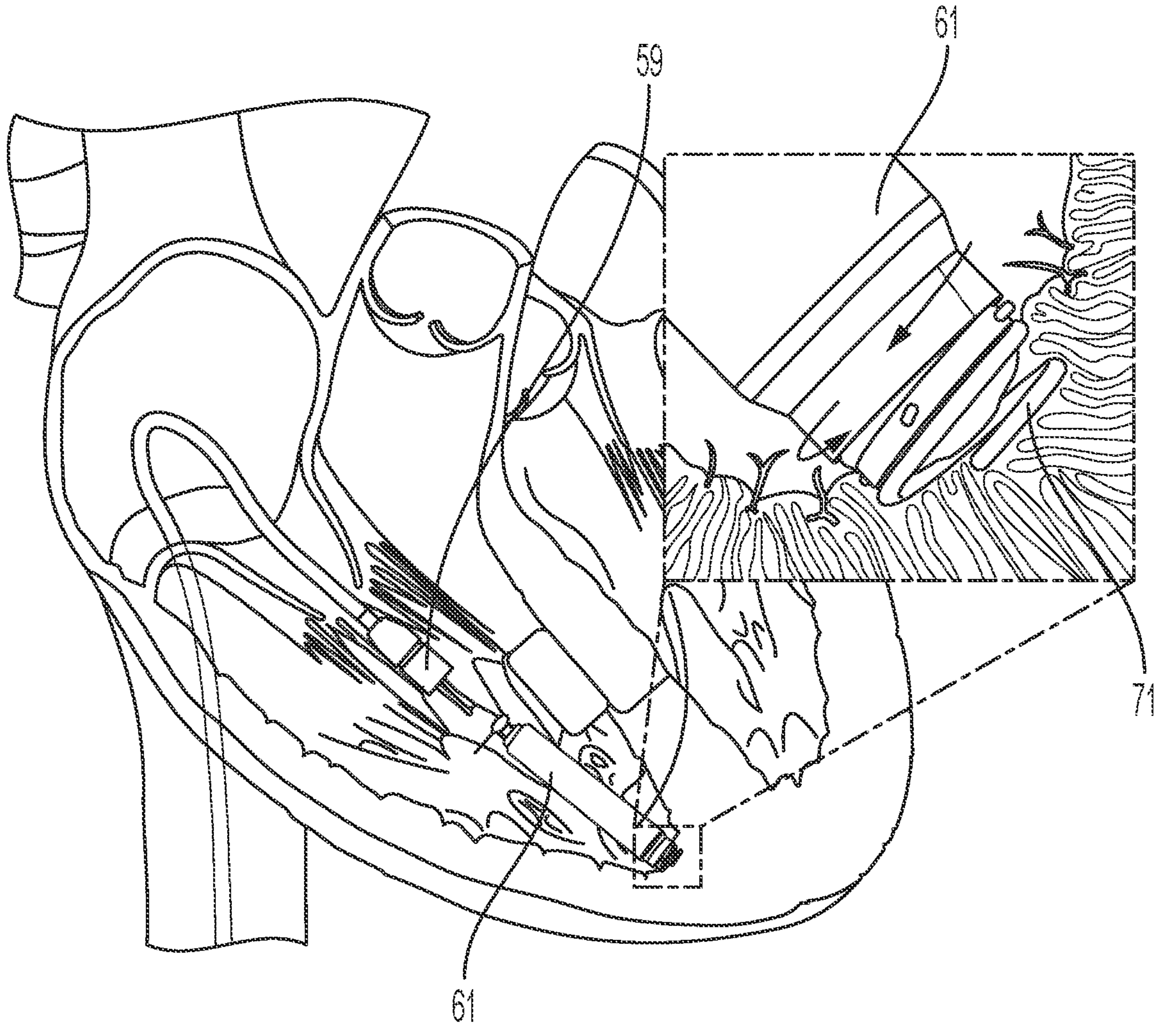
FIG. 3 is an illustration of a sensing device in accordance with embodiments implanted in a right ventricle of a patient's heart.

FIG. 2 is a diagrammatic illustration of a medical system 60 in accordance with embodiments for determining a treatment regimen for a patient with a heart condition such as left heart failure, right heart failure or primary pulmonary disorder. As shown, the medical system 60 includes a sensing device 61 (i.e., a measurement device) and a monitoring system 62. As described in greater detail below, the sensing device 61 includes a pressure sensor (not shown in FIG. 2) configured to be implanted in a right ventricle of a patient's heart. FIG. 3 is an illustration of an embodiment of the sensing device 61 where the entire sensing device is located and implanted in a right ventricle of a patient's heart. For example the sensing device 61, or at least the pressure sensor, may be implanted in the right ventricle free wall, right ventricle apex, right ventricle septum or right ventricle outflow tract. The sensing device can be delivered and implanted into the right ventricle using conventional methods such as trans-catheter delivery (e.g., by a delivery catheter 59 through vasculature including the vena cava, right atrium, pulmonary valve and into the right ventricle), or open heart surgical approaches. Following implantation of the sensing device 61, room may remain in the right ventricle for other structures such as pacing leads, wireless pacemakers, CRT leads, ICD leads, leadless pacemakers, etc., or combined with the leads of wireless pacemakers. These and other structures of these types can be used in combination with the sensing device 61 and methods described herein. For example, pacemakers and/or ICDs may be used as an input for the ECG signal used to identify right ventricular end diastolic (RVEDP) and right atrial pressures in accordance with embodiments described herein.

The sensing device 61 monitors pressures in the patient's right ventricle over periods of time (e.g., one or more heartbeats or cycles of diastole and systole). Monitoring system 62 is coupled to receive data or information representative of the measured right ventricle pressures (referred to as RVP information in this description). In embodiments, monitoring system 62 is configured to wirelessly receive the RVP information transmitted by the sensing device 61. Monitoring system 62 is also configured to process the received RVP information, and to determine a right atrial filling pressure (RAP) of the patient's heart based on the RVP information, and to determine a left atrial filling pressure (LAP) of the patient's heart based on the RVP information. As described in greater detail below, embodiments of the monitoring system 62 determine both the right atrial filling pressure and the left atrial filling pressure of the patient's heart using the right ventricular pressure represented by the RVP information as a surrogate. Embodiments of the monitoring system 62 include a display device (not shown in FIG. 2) that displays the determined right atrial filling pressure and the determined left atrial filling pressure. Embodiments of the monitoring system 62 may be configured to determine and display the heart condition of the patient and/or a treatment regimen for the patient based at least in part on the determined right and left atrial filling pressures of the patient.

Figure 4:
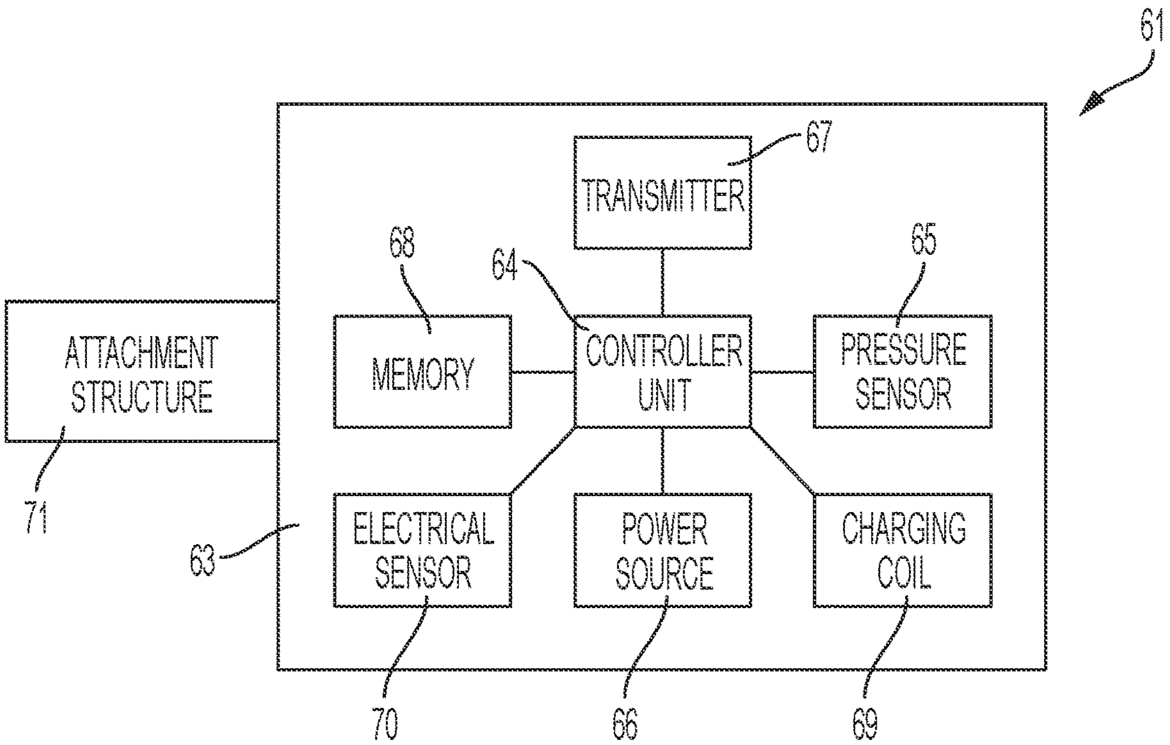
FIG. 4 is a diagrammatic illustration of a sensing device in accordance with embodiments.

FIG. 4 is a diagrammatic illustration of a sensing device 61 in accordance with embodiments. The illustrated embodiments include a housing 63 enclosing a controller unit 64 coupled to components including pressure sensor 65, power source 66, transmitter 67, memory 68, charging coil 69 and electrical sensor 70. An attachment structure 71 on the housing 63 may be used to anchor the sensing device 61 to tissues of the patient's heart (e.g., at a bottom portion of the right ventricle as shown in FIG. 3). Housing 63 can be formed of appropriate known or otherwise conventional materials such as biocompatible metal (e.g. stainless steel or titanium) and/or polymers. Controller unit 64 may be embodied in suitable known or otherwise conventional electronics structures such as discrete circuit components, application specific integrated circuits (ASICs) or programmed processors. Similarly, memory 68 may be embodied in suitable known or otherwise conventional structures configured for operation with the controller unit 64. Pressure sensor 65 may, for example, incorporate MEMS technology such as but not limited to capacitive or piezoelectric sensors or other pressure measurement technologies suitable for measurement of intracardiac pressure levels. Signals or other information representative of pressures monitored by the pressure sensor 65 (e.g., the RVP information) are coupled to controller unit 64 and may optionally be stored in the memory 68. In other embodiments (not shown), components of the sensing device 61 other than the pressure sensor 65 may be located outside of the patient's heart, (e.g., in a housing located under the skin in the patient's chest) and coupled (e.g., by leads) to an implanted pressure sensor 65.

Embodiments of the transmitter 67 include an antenna (not separately shown) to wirelessly transmit the RVP information provided by the controller unit 64 (e.g., by radio frequency (RF)). Embodiments of transmitter 67 may, for example, include near field (e.g., Bluetooth) or other suitable known or conventional technologies. Power source 66 may be any suitable source. In embodiments, the power source 66 includes the charging coil 69 coupled to an energy storage device to enable inductive charging of the power source by an external device. In embodiments including such an inductive power source 66, the sensing device 61 can be energized by the external device and thereby operated to measure the right ventricular pressure and transmit the RVP information. In inductive charging embodiments of this type the sensing device 61 may measure pressure and transmit the RVP information only when the power source 66 is energized. An advantage of such an inductive charging power source 66 is that the need to exchange the power source when it runs out of power is reduced. The charging coil 69 and the antenna of the transmitter 67 may be the same structure in embodiments having an inductive charging power source 66. Alternatively or in addition, embodiments of power source 66 may include a battery.

The illustrated embodiment of sensing device 61 includes electrical sensor 70. The electrical sensor 70 is configured to measure and provide signals representative of electrical activity of the heart. In embodiments, for example, electrical sensor 70 may measure and provide information representative of electrocardiogram (ECG) signals in the patient's heart. Embodiments of the electrical sensor 70 may include anode and cathode terminals on the housing 63 (not separately shown). The electrical information measured by the electrical sensor 70 is coupled to the controller unit 64 and may be transmitted by the transmitter 67. The electrical information measured by electrical sensor 70 may also be stored in the memory 68. Other embodiments of sensing device 61 and/or the medical system 60 do not include an electrical sensor such as 70. As described below, some embodiments of medical system 60 do not make use of electrical information such as the ECG of the heart. Yet other embodiments of medical system 60 make use of electrical information such as the ECG of the patient's heart that are obtained from other sources (e.g., electrodes on the patient's body and/or other implanted devices in the patient).

Figure 19:
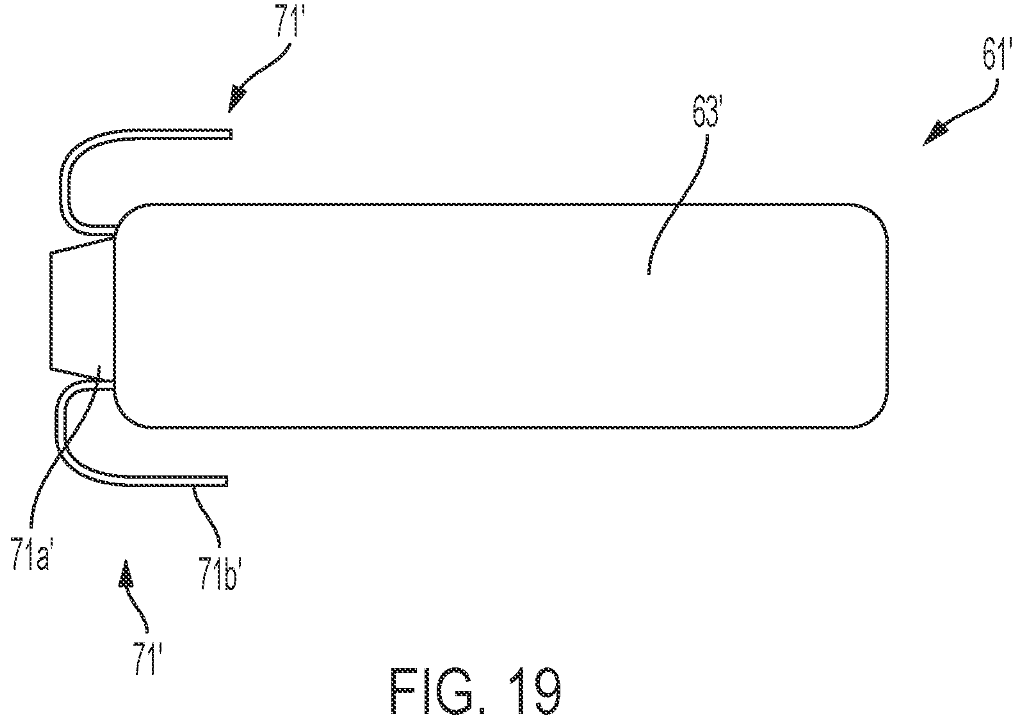
FIG. 19 is an illustration of another sensing device including an attachment structure in accordance with embodiments.

Attachment structure 71 may include known or otherwise conventional structures to anchor the sensing device 61 (or pressure sensor 65 in embodiments) within the right ventricle of the patient's heart. In the embodiments shown in FIG. 3, for example, attachment structure 71 includes helically coiled springs configured to engage and enter the heart tissue upon rotation of the sensing device 61. Other embodiments of attachment structure 71 include other structures, such as for example one or more hooks optionally including barbs. FIG. 19, for example, illustrates a sensing device 61' including a plurality of anchors 71' (two are shown for purposes of example) configured to secure the sensing device under a tissue surface in a patient's right ventricle. In the illustrated embodiments each of anchors 71' includes a substantially linear section **71*a*' extending from a distal end of the housing 63' generally parallel to a longitudinal axis of the housing, and a curved section 71*b*' extending from the substantially linear section. The curved section 71*b*' of each anchor 71' may be configured to align with the substantially linear section 71*a*' relative to the longitudinal axis of the housing 63'** in a delivery configuration, and curve radially outwardly relative to the longitudinal axis and toward the distal end of the housing in the deployed configuration.

Figure 5:
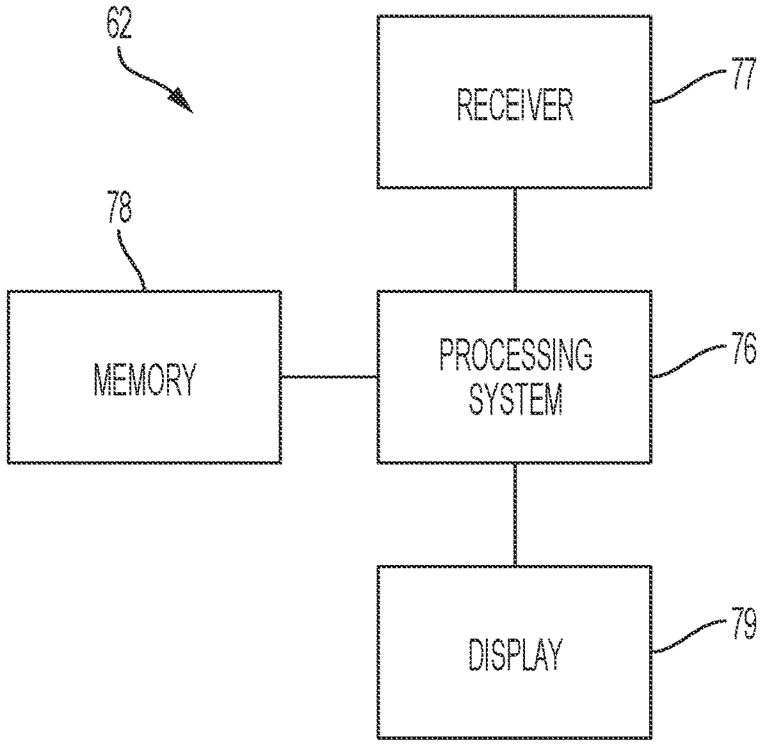
FIG. 5 is a diagrammatic illustration of a monitoring device in accordance with embodiments.

FIG. 5 is a diagrammatic illustration of a monitoring system 62 in accordance with embodiments. The illustrated embodiments include a processing system 76 coupled to a receiver 77, memory 78 and display 79. Processing system 76 is a programmable microprocessor-based system in embodiments. Memory 78, which can for example include ROM and RAM, is coupled to the processing system 76 and can store data and information such as programs executed by the processing system. For example, and as described in greater detail below, processing system 76 can execute programs stored in memory 78 that characterize methods or algorithms to generate the right atrial filling pressure and the left atrial filling pressure in the patient's heart based on the RVP information transmitted by the sensing device 61. Processing system 76 may also execute programs stored in memory 78 to determine heart conditions and treatment regimens based on information such as the right atrial filing pressure and left atrial filling pressure of the patient's heart in accordance with methods and algorithms described below. Alternatively or in addition, processing system 76 can be implemented by other suitable structures such as discrete circuit elements and ASICs. In embodiments, monitoring system 62 can be embodied as an app (i.e., application software) in a conventional mobile device such as a smartphone or tablet. In other embodiments all or components of monitoring system 62 (e.g., processing system 76, memory 78 and display 79) can be embodied as a "desktop" computer system coupled to a receiver 77 (e.g., over a communications network). Yet other embodiments of monitoring system 62 include computing components in the cloud coupled to a user's device, such as a mobile phone or tablet, including a display.

Receiver 77 is configured to receive information such as the RVP information from the sensing device 61, and to couple the received information to the processing system 76. Receiver 77 wirelessly receives the information in embodiments (e.g., by RF). In embodiments that make use of ECG or other electrical information of the patient's heart, the electrical information may also be received by and coupled to the processing system 76 by the receiver 77.

Display 79 can be operated by the processing system 76 to display information received by and/or generated by the processing system. In embodiments, for example, the display 79 can display one or more of the RVP information, the right atrial filling pressure and/or left atrial filling pressure, determined heart conditions, determined treatment regimens and/or heart electrical information. Display 79 can also be configured to display other information measured or otherwise obtained from the patient, such as for example blood pressure, temperature and/or oxygen saturation. If the patient is visually impaired or prefers audio notifications, the monitoring system 62 can provide audio output to alert the patient if measurements indicate the patient's heart may be a risk of acute decompensation episodes, so that the patient can go to a hospital for further examination. The monitoring system 62 can also upload the measured and/or generated data and information onto a remote server (not shown) to be collected by medical service providers or a database to remotely monitor the conditions of the patient's heart.

Figure 6:
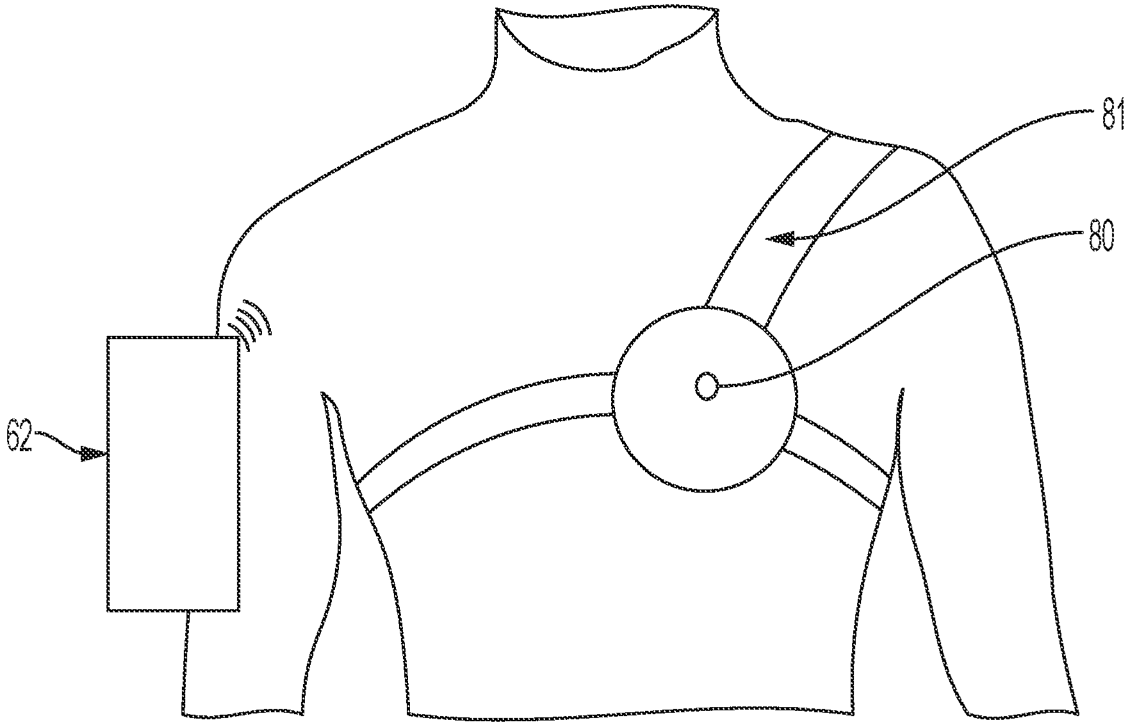
FIG. 6 is an illustration of an external charger and communication relay in accordance with embodiments.

FIG. 6 shows an example of an external charger and communications relay 80 according to some examples. As shown, the external charger and communications relay 80 is a device which can charge or power a power source such as 66 of the sensing device 61 (for example, a battery or capacitor) via electromagnetic induction, as well as to communicate with the sensing device to obtain measurement data or information such as the RVP information. In one example, the external charger and communications relay 80 is a device which inductively couples with the sensing device 61 to directly power the sensing device such that an on-board power source, for example a battery, is not required. In one example, the external charger and communications relay 80 wirelessly powers the sensing device 61 via radiofrequency (RF) electromagnetic radiation. The external charger and communications relay 80 may be worn (e.g., using a harness 81) such that the location of the charger and relay 80 is placed at an operable location for the charger and relay to charge and obtain data from the sensing device 61. Monitoring system 62 can be used by the patient or other party (e.g., medical service provider or remote monitoring facility) to receive information regarding the measurement data via the external charger and communications relay 80. In other embodiments data and other information measured by the sensing device 61, including the RVP information, can be transmitted by the sensing device directly to the monitoring system 62 (e.g., if the sensing device is battery powered).

Figure 7A:
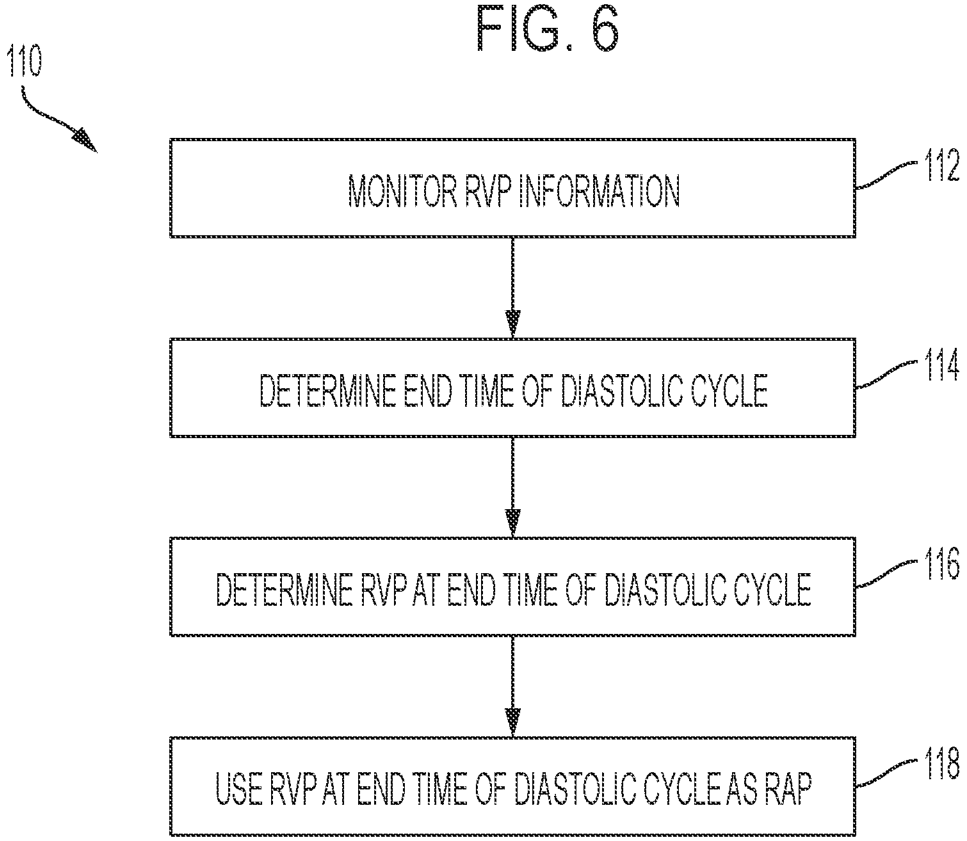
FIG. 7A is a flow diagram describing a method for determining right atrial filling pressures from right ventricle pressure information in accordance with embodiments.
Figure 7B:
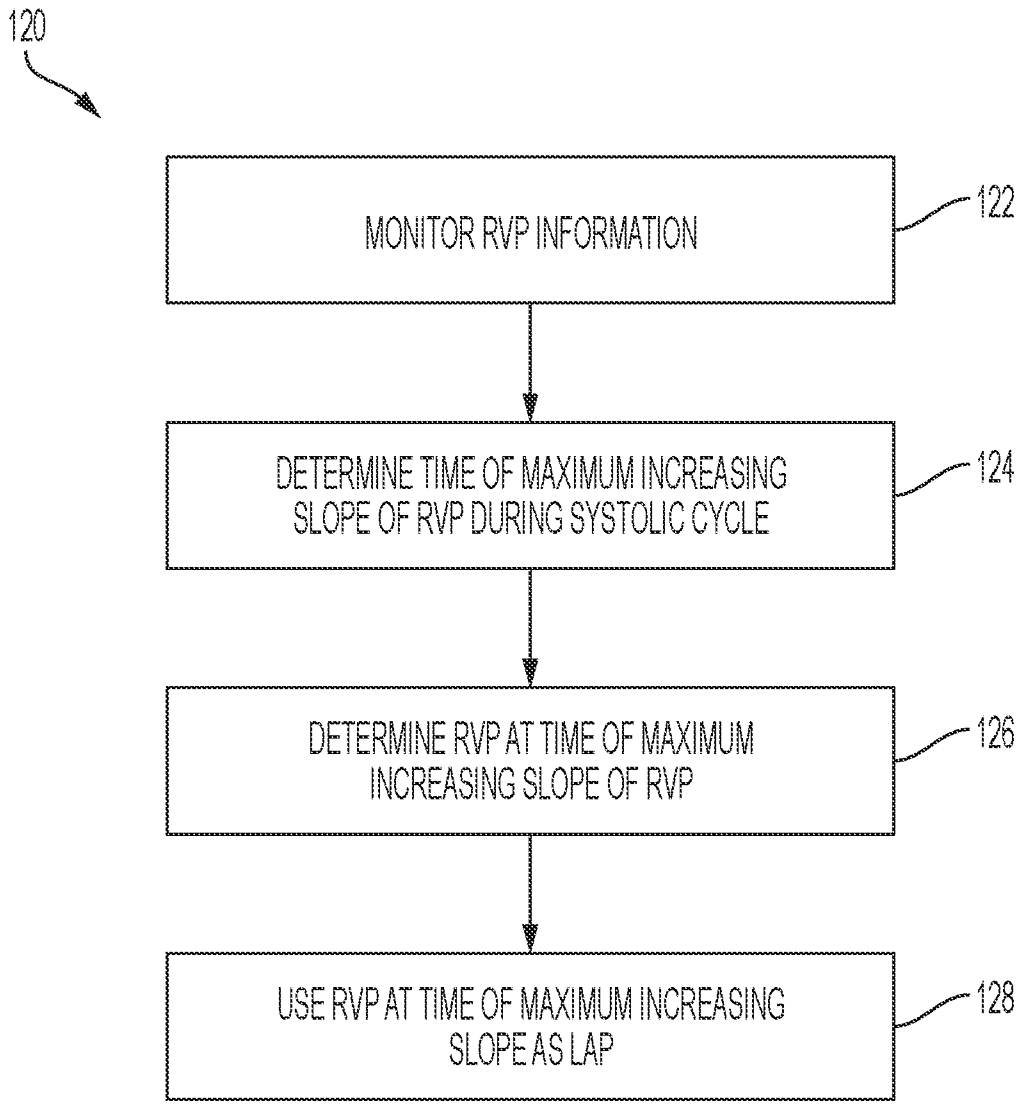
FIG. 7B is a flow diagram describing a method for determining left atrial filling pressures from right ventricle pressure information in accordance with embodiments.
Figure 18:
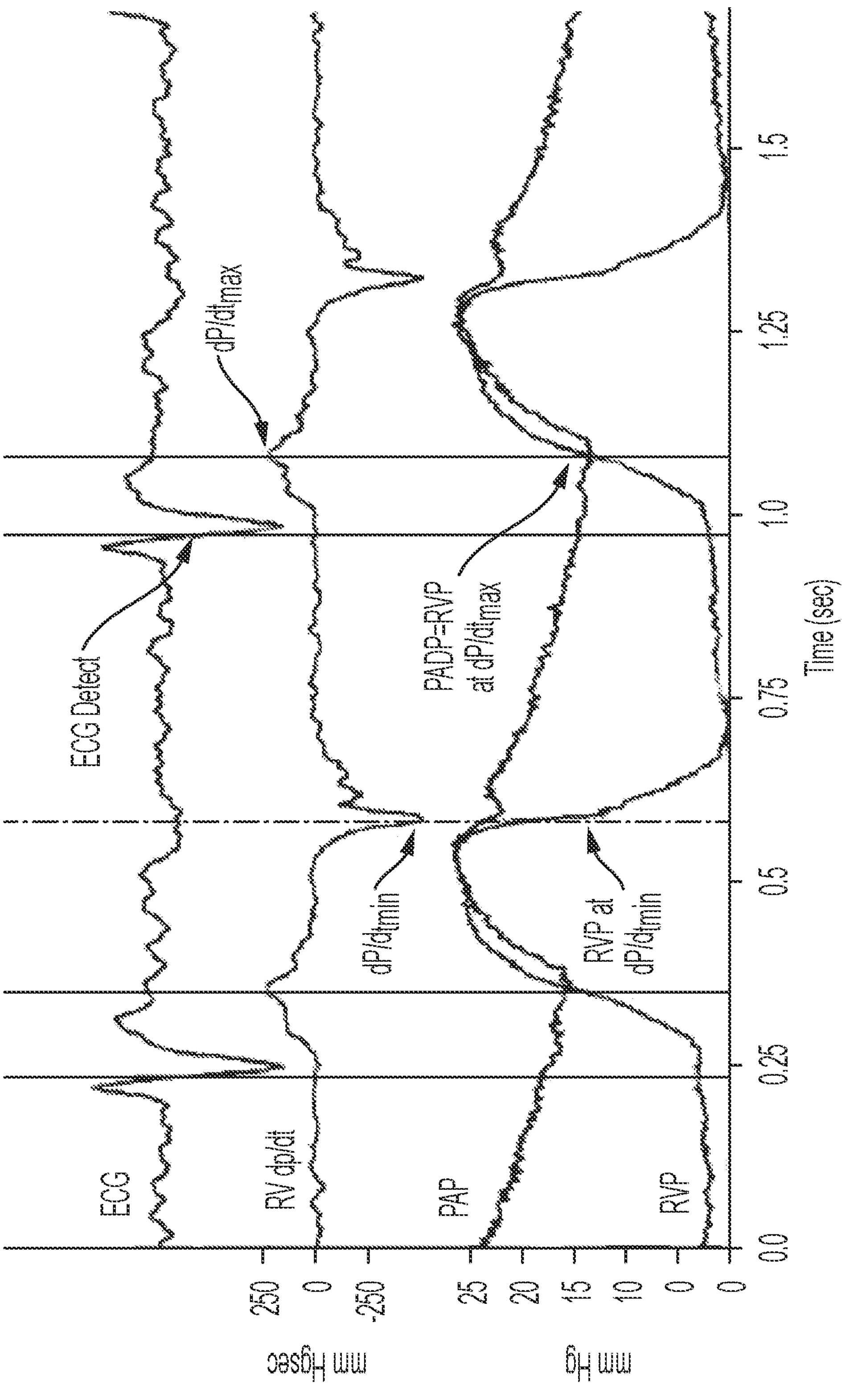
FIG. 18 is a graph of an exemplary RVP (right ventricular pressure) over several diastolic and systolic heart cycles, and associated pulmonary arterial pressure (PAP), RV dp/dt (right ventricular pressure changes over time), and ECG (electrocardiogram)

FIGS. 7A and 7B are flowcharts illustrating methods and algorithms that can be implemented by the monitoring system 62 using the RVP information, and optionally the heart electrical information, to generate or determine the patient's right atrial filling pressure and left atrial filling pressure. FIG. 18 is a graph of an example of right ventricular pressures (RVP) monitored within a patient over a period of time including two diastolic and systolic cycles. The RVP information used by the methods of FIGS. 7A and 7B can be data or other information representative of the illustrated right ventricular pressure. FIG. 18 also illustrates exemplary pulmonary artery pressures (PAP), changes in the right ventricular pressures over time (i.e., slopes) (RV dP/dt) and ECG signals of the patient, that are associated with and correspond to the right ventricular pressure RVP. The pressures, changes in pressures and electrical signals shown in FIG. 18 are used in connection with the description of the methods shown in FIGS. 7A and 7B. In embodiments, the data acquisition frequency of sensing device 61 is greater than 100 Hz to determine the maximum dP/dt for purposes of obtaining estimated pulmonary artery diastolic pressure (ePAD). In embodiments, for example, the data acquisition frequency is 200 Hz-250 Hz, or even greater. If the data acquisition frequency is too low, accuracy of the determinations or locations for ePAD on the right ventricular pressure waveform, as represented by the RVP information, may be detrimentally impacted.

Method 110 illustrated in FIG. 7A uses the right ventricular pressures RVP, as represented by the RVP information, as surrogates for determining the right atrial filling pressure. Right atrial filling pressure or right atrial pressure (RAP) is generally equal to the right ventricle end diastolic pressure (RVEDP), which is the right ventricle pressure at the end of the diastolic cycle of the heart (e.g., in the absence of tricuspid valve issues). Accordingly, by method 110 the monitoring system 62 monitors the RVP information as shown by step 112, and determines the end time of the diastolic cycle as shown by step 114. The end of the diastolic cycle during which the right ventricle fills with blood defines the beginning of the systolic cycle during which the heart contracts to pump deoxygenated blood from the right ventricle through the pulmonary valve toward the lungs. Accordingly, and as shown in FIG. 18 at the times corresponding generally to 0.25 sec. and 1.0 sec., the right ventricular pressure RVP, and therefore the RVP information, relatively quickly and substantially increase immediately following end diastole. As is also shown in FIG. 18, the ECG signal relatively quickly and substantially decreases at the beginning of the systolic cycle. Method 110 can make use of these physiologic and/or electrical characteristics of the heart in connection with step 114.

In one embodiment the monitoring system 62 monitors the slope of the RVP information to determine the end time of the diastolic cycle as shown by step 114. For example, the monitoring system 62 can identify the end time of the diastolic cycle as the time that the slope of the RVP information increases by a predetermined amount (e.g., exceeds a threshold value) within a predetermined time period. As shown by steps 116 and 118, monitoring system 62 then determines the right ventricular pressure at the determined end time of the diastolic cycle, and uses the right ventricular pressure at the end of the diastolic cycle as the right atrial pressure. By this embodiment, the monitoring system 62 can determine the right atrial filling pressure without the use of the ECG or other electrical information. This embodiment can thereby be implemented using a sensing device 61 that does not include an electrical sensor such as 70 (as shown for example in the embodiment in FIG. 4).

In embodiments where the monitoring system 62 receives heart electrical information such as the ECG (e.g., embodiments having a sensing device 61 including electrical sensor 70), monitoring system 62 may use the electrical information to determine the end time of the diastolic cycle by step 114. For example, the monitoring system 62 can identify the end time of the diastolic cycle as the time that the slope of the ECG information decreases by a predetermined amount (e.g., exceeds a threshold value) within a predetermined time period. Monitoring system 62 then determines the right ventricular pressure at the determined end time of the diastolic cycle, and uses the right ventricular pressure at the determined end time of the diastolic cycle as the right atrial pressure as shown by steps 116 and 118. Conventional signal processing approaches including slope determinations and detection, filtering, comparisons and thresholding can be used in connection with these embodiments of method 110. By this method 110 the monitoring system 62 determines the right atrial filling pressures without directly monitoring pressure in the right atrium (e.g., there is no pressure sensor in the right atrium). Instead, the right atrial pressures are determined using heart pressure information consisting only of the RVP information. Other embodiments may use other signal processing approaches and algorithms to determine the right atrial filling pressures based on the RVP information. For example, in other embodiments, obtaining right atrial filling pressures based on the RVP waveforms may be performed using the systems and methods described in U.S. Pat. No. 6,915,162, entitled, "Implantable Medical Device For Measuring Ventricular Pressure," and issued on Jul. 5, 2005, the entire contents of which is incorporated herein in its entirety for all purposes. Additionally, or alternatively, in other embodiments, obtaining right atrial filling pressures based on the RVP waveforms and/or ECG information may be performed using the systems and methods described in U.S. Pat. No. 5,368,040, entitled, "Apparatus And Method For Determining A Plurality Of Hemodynamic Variables From A Single, Chronically Implanted Absolute Pressure Sensor," and issued on Nov. 29, 1994, the entire contents of which is incorporated herein in its entirety for all purposes.

Method 120 illustrated in FIG. 7B uses the right ventricular pressures RVP, as represented by the RVP information, as surrogates for determining the left atrial filling pressures (LAP). The left atrial pressure is generally equal to the estimated pulmonary artery diastolic pressure (ePAD or PADP). The pulmonary artery diastolic pressure is generally equal to the right ventricular pressure at the time of the pulmonary valve opening. The pulmonary valve opens at a time generally corresponding to the time of maximum or peak increasing pressure change or slope in the right ventricular pressure during systole. Accordingly, by method 120, the monitoring system 62 monitors the RVP information as shown by step 122, and determines the time at which the RVP has its maximum increasing change or increasing slope (dP/dt) during the systolic cycle as shown by step 124. As shown by steps 126 and 128, the monitoring system 62 then determines the right ventricular pressure at the time of maximum change of the RVP slope (which corresponds to the pulmonary artery diastolic pressure at the time of the pulmonary valve opening), and uses that right ventricular pressure as the left atrial pressure LAP. In embodiments, the right ventricular pressure RVP at the time at which the RVP has its minimum slope (dP/dt) during the systolic cycle can also be used as a surrogate for the left atrial filling pressure LAP (e.g., in addition to or as an alternative to the approaches described above). FIG. 18 is annotated, for example, to show a minimum slope of RVP (dP/dt min) and the associated RVP. Conventional signal processing approaches including slope determinations and detection, filtering, comparisons and thresholding can be used in connection with these embodiments of method 120. By this method the monitoring system 62 determines the left atrial filling pressures without directly monitoring pressure in the left atrium (e.g., without the use of a pressure sensor in the left atrium). Instead, the left atrial pressures are determined using heart pressure information consisting only of the RVP information. Other embodiments may use other signal processing approaches and algorithms to determine the left atrial filling pressures based on the RVP information.

In other embodiments, the sensing device 61 is configured to determine the right atrial pressures and left atrial pressures using the RVP information. Embodiments of a sensing device 61 of these types can, for example, include a processing system such as 76 that processes the RVP information in accordance with methods 110 and 120. In embodiments of these types, the sensing device 61 can transmit or otherwise couple the determined right and left atrial pressures to the monitoring system 62.

In embodiments, the sensing device 61 and/or monitoring system 62 can be used in combination with other medical devices. Examples of such medical devices include, but are not limited to, blood pressure cuffs, pulse-oximeters, scales, creatinine testing devices, smart devices, and wearable medical tracking devices, to name a few. The sensing device 61 can also be combined with other implantable devices, such as for example a ventricular assist device (VAD), drug delivery shunt or system. The sensing device 61 may provide feedback to the other implantable device(s), as part of a closed loop or open loop feedback system. The VAD may be a right VAD, a left VAD, or a bi VAD.

The pressure measurement data obtained using the sensing device 61 as described herein can be used to perform pulse-contour method, which is another method that is used to measure the cardiac output of the patient. This method uses the continuous pressure measurement data to plot a pressure-versus-time graph for the patient's heart, after which the pressure integral, i.e. the area beneath the plotted line on the pressure-versus-time graph, is used to determine the stroke volume (SV) of the portion of the heart that is being measured. The value of SV multiplied by the heart rate is the cardiac output.

Figure 8:
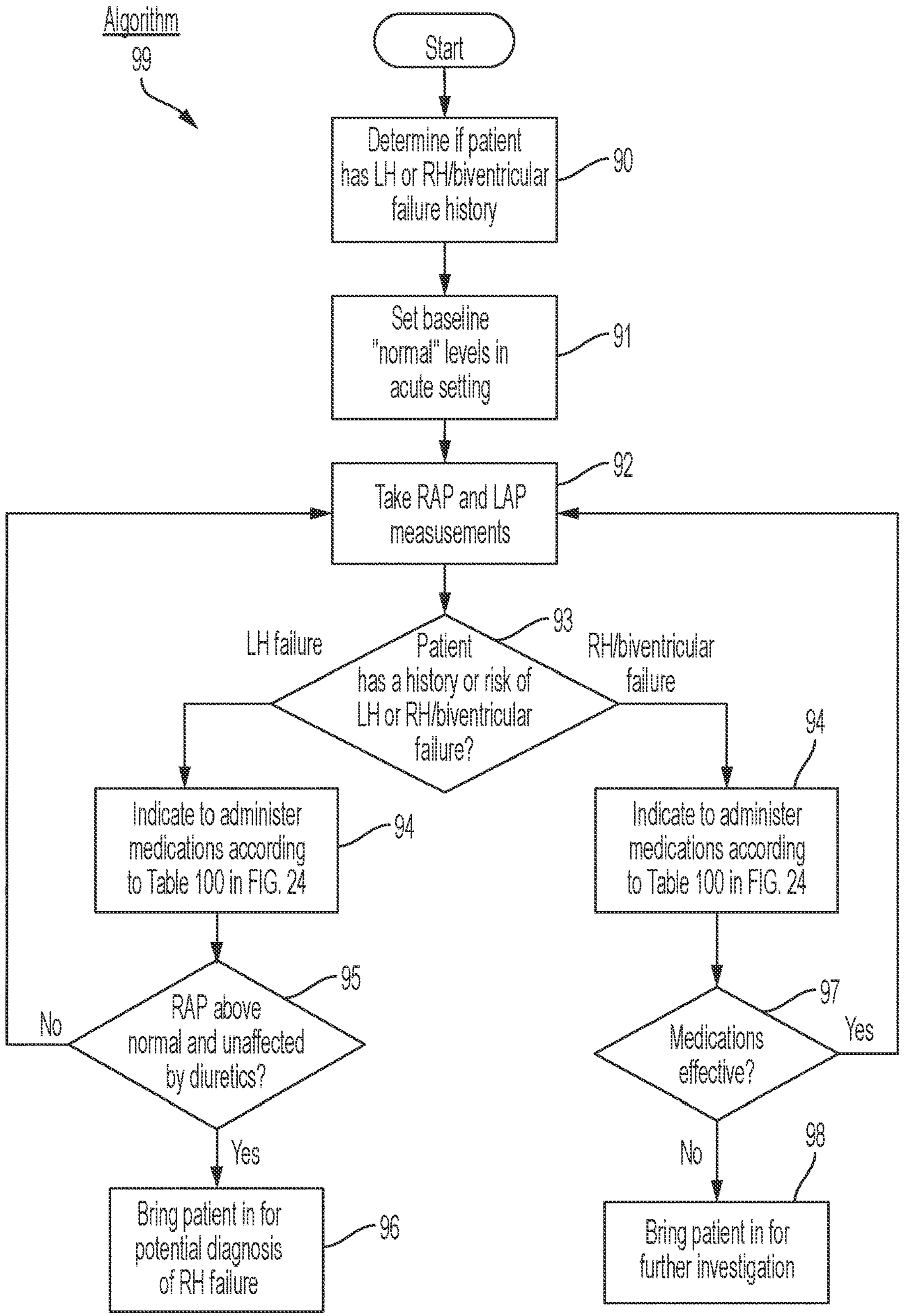
FIG. 8 illustrates a block diagram of a method to determine actions that need to be taken based on pressure measurements according to some embodiments.

FIG. 8 is a flow chart showing a remote medical treatment monitoring method 99 that can be implemented using one or more electronic devices, such as the monitoring system 62, using measurement data received from the sensing device 61, for example, or any of the sensor elements described herein (e.g., RAPs and LAPs determined as described herein). In some examples, the method 99 is used for patients with a history of left heart failure (LHF), to determine treatment protocols guided by measured right and left heart physiologic metrics (e.g., pressure, temperature, and/or oxygen saturation).

Regardless, in some embodiments, in an optional first step 90 the service provider determines if the patient receiving treatment has a history of either left heart (LH) or right heart (RH)/biventricular failure. The method 99 may be used for patients with a risk of LH or RH/biventricular failure as determined by the medical service providers, regardless of history. In optional step 91, the medical service provider set a baseline "normal" level for applicable physiologic metrices (e.g., the left and right atrial pressures) in the acute setting by performing various tests on the patient to determine, based on the current condition of the patient, what normal levels (pressure, cardiac output, and/or oxygen saturation) would be. Baseline values can then be entered into the system which transfers the data to the monitoring system 62. In the example illustrated in this figure, the pressures being measured are the left atrial pressure (LAP) and the right atrial pressure (RAP). Other embodiments may include other measurements of other parts of the heart, as deemed appropriate by the medical service provider.

In some examples, the monitoring system 62 receives or determines RAP and LAP measurements in step 92. In one implementation, the measurements include whether the pressure values of the right atrium and the left atrium are trending below, at, or above the normal level. In another example, the method may also consider whether the pressure values are increasing, decreasing, or staying steady as an additional input into the overall assessment.

In optional step 93, the monitoring system 62 confirms whether the patient has a history of LH or RH/biventricular failure. The monitoring system 62 optionally uses a medication administration reference table 100 in FIG. 9 to determine and indicate if dosage of certain medications needs to be increased or reduced, in step 94. Alternatively, a medical service provider (e.g., physician) optionally uses the data directly to assess what treatment regimen (e.g., pharmacological) is appropriate based upon the data using the methodology of table 100.

As shown, the table 100 has three columns and three rows, where the columns pertain to "RAP trending below normal" 101, "RAP trending normal" 102, and "RAP trending above normal" 103, and the columns pertain to "LAP trending below normal" 104, "LAP trending normal" 105, and "LAP trending above normal" 106. For example, if the RAP is trending below normal but the LAP is trending above normal, the method would include the step of "Increase Vasodilators" according to the table 100. If automated, a consistent "message" or communication could be relayed to a user of the monitoring system. On the other hand, if the RAP is also trending above normal, the method would include the step of "Increase Diuretics". Again, if automated, a consistent "message" or communication could be relayed to a user of the monitoring system. It should be noted that when the LAP and RAP values are both in the normal level (i.e. the box defined by the "LAP normal" row and "RAP normal" column), one method would include not altering any medications.

After the initial medication is administered, the method 99 includes verifying to see if the RAP is still trending above normal and if the RAP value is unaffected by diuretics, in step 95. This may occur in the second example shown above, where the LAP and RAP are both trending above normal, so the amount of diuretics administered to the patient is increased, but a subsequent measurement of the RAP shows that this pressure is still above normal. In this instance, the monitoring system 62 could display an indication in step 96 instructing the medical service provider to bring the patient in for a potential diagnosis of RH failure (or the medical service provider could carry out the step 96 based upon the data). Among other possible causes of high RAP is primary pulmonary arterial hypertension. When the medical service provider tests the patient for possible diagnosis of these conditions, the medical service provider can set a new baseline value range for the "RAP normal" level and update the patient's status as having a history of RH/biventricular failure so that moving forward, the method will proceed to step 97 instead of step 95 in the future. Otherwise, if the RAP decreases to the normal level, the monitoring system 62 optionally goes back to step 92 to take subsequent RAP and LAP measurements.

Returning to step 93, if the monitoring system 62 (or the medical service provider) confirms that the patient has a history of RH/biventricular failure, the method 99 proceeds to step 97 after determining which medication to increase or decrease based on analysis outlined in table 100. In step 97, the method 99 includes determining if the medication administered in step 94 is effective. For example, the method 99 may include comparing the previous LAP and RAP values with the new LAP and RAP values taken after the medication is administered. If the comparison shows that there is an insufficient change in the status in a way that indicates that the administered medication is ineffective (for example, if the LAP or RAP is still below normal and the medication is not causing it to increase toward normal level, or if the LAP or RAP is still above normal and the medication is not causing it to decrease toward normal level, etc.) the medical service provider may bring the patient in for adjusted treatment and/or the monitoring system 62 may provide a message or other communication indicating that further diagnosis/treatment is warranted in step 98. The possible lack of efficacy of the medications may be a sign of increased exigency or that immediate medical attention is otherwise warranted. Otherwise, if the administered medication is showing apparent efficacy in moving LAP and RAP toward nominal or desired levels, the method returns to step 92 and the monitoring system 62 continues to receive and evaluate new measurements for assessing patient health.

Use of at least two sets of measurement data (in this example, LAP and RAP measurements) obtained by the devices and methods described herein in assessing cardiac function is advantageous over prior-art methods with only one set of measurement data for a variety of reasons, including that the second set helps facilitate more accurate root cause diagnosis and treatment.

In another embodiment, the method 99 may be programmed so that instead of using the actual measured LAP and RAP values, a ratio of LAP to RAP (or a ratio of RAP to LAP) may be used to determine which medications to administer and how much. This methodology may be based on the understanding that the pressures within the left and right atria should correspond to a desired ratio (e.g., 2:1 LAP:RAP) in a healthy heart, therefore the ideal ratio of LAP to RAP can be determined (e.g., an ideal ratio of 2:1 pressures are desired), and any ratio that is significantly smaller or larger than the desired ratio (e.g., 2:1) would pose a threat to the patient's health.

In some examples, if the ratio of LAP to RAP is above a threshold value (i.e. the LAP is much higher than the RAP) and keeps increasing in a patient with a history of LH failure, the method may include a determination that the amount of vasodilators being administered should be increased. The threshold ratio value of LAP to RAP which triggers such a determination may be determined and updated periodically by the medical service provider (e.g., after examination performed on the patient). In other words, various methods include one or more medical service providers determining the range of "normal" baseline ratios, which will then be used in the medication administration reference table. Alternatively, a generalized set of guidelines may be provided to medical service providers regarding an appropriate baseline.

The method 99 can be adjusted to be more specific in terms of how much a pharmacological, or medication regimen needs to be increased or reduced, which can be varied based on how much the LAP and RAP are trending above or below the normal level. This may be done by implementing another table or set of guidelines within the table 100 that indicates the amount of medication to be administered (e.g., so that a treatment dosage may be adjusted for a patient without requiring direct medical service provider intervention). The table 100 can include any of a variety of medical recommendations/indications, such as beta-blockers and inotropes, for example, as indicated by a particular set of physiologic measurements and associated guidance of the table 100. Furthermore, to inform the patient on which medication to choose and its dosage, the type of medication (e.g. diuretic or vasodilator) that needs to be administered and the dosage thereof can be displayed on, for example, the screen of a computer or a display of a smart device used by the patient.

As referenced above, the measurement data and associated monitoring and treatment methodology is not necessarily limited to LAP and RAP measurements. In some examples, additional or alternative locations (e.g., pulmonary arteries, ventricles, pulmonary veins, aorta, and others) and/or additional or alternative metrics (e.g., temperature and/or oxygen saturation) may be utilized in implementing a monitoring and treatment method such as the method 99.

As explained above, the method 99 may be performed manually or may be partially or completely automated using any device capable of receiving and processing the measurement data from the sensing device 61. For example, the method 99 may be implemented entirely in the monitoring system 62 (e.g., such as a smart device), which performs all the comparisons, calculations, and determinations after receiving the LAP and RAP measurement data from the sensing device 61. In some examples, the method may be implemented partially in the monitoring system 62 and partially in the communications relay 80 which may include a processing unit to receive the LAP and RAP measurement data from the pressure sensor, determine whether the LAP and RAP are above/at/below normal level and decreasing/steady/increasing, then relay this information to the monitoring system 62 to perform the rest of the method. In yet another example, the sensing device 61 may have appropriate structure and be programmed to perform a portion or the entirety of the method.

In still further examples, the method 99 may be implemented in a device with a user interface allowing the patient to administer medications according to the results of the method. The method may also be implemented in the medical service providers' electronic health record (EHR) or electronic medical record (EMR) systems which keep track of the necessary records of each patient. As such, the EHR or EMR systems may use local or remote database to access, among other things, the patient's history of LH or RH/biventricular failure and whether the medical service providers have deemed the patient to be at a risk of such failure. The resulting data from the method may be displayed on a dashboard of the user interface with multiple options for the user (e.g. patient and medical service providers), which may include: LAP and RAP averages, trend arrows, line graphs over time, and waveforms, as well as a history of the medications taken by the patient, etc. The dashboard may also be configured such that the user can first pull up the most meaningful information, such as the averages and trends, then dig in further for a more detailed analysis, such as the waveforms. This may be implemented by organizing the multiple options in a hierarchical manner based on the importance of each option. In one example, this hierarchical order of the options is customizable according to the user's preference, such that the most preferred information can be pulled up first.

Figure 10:
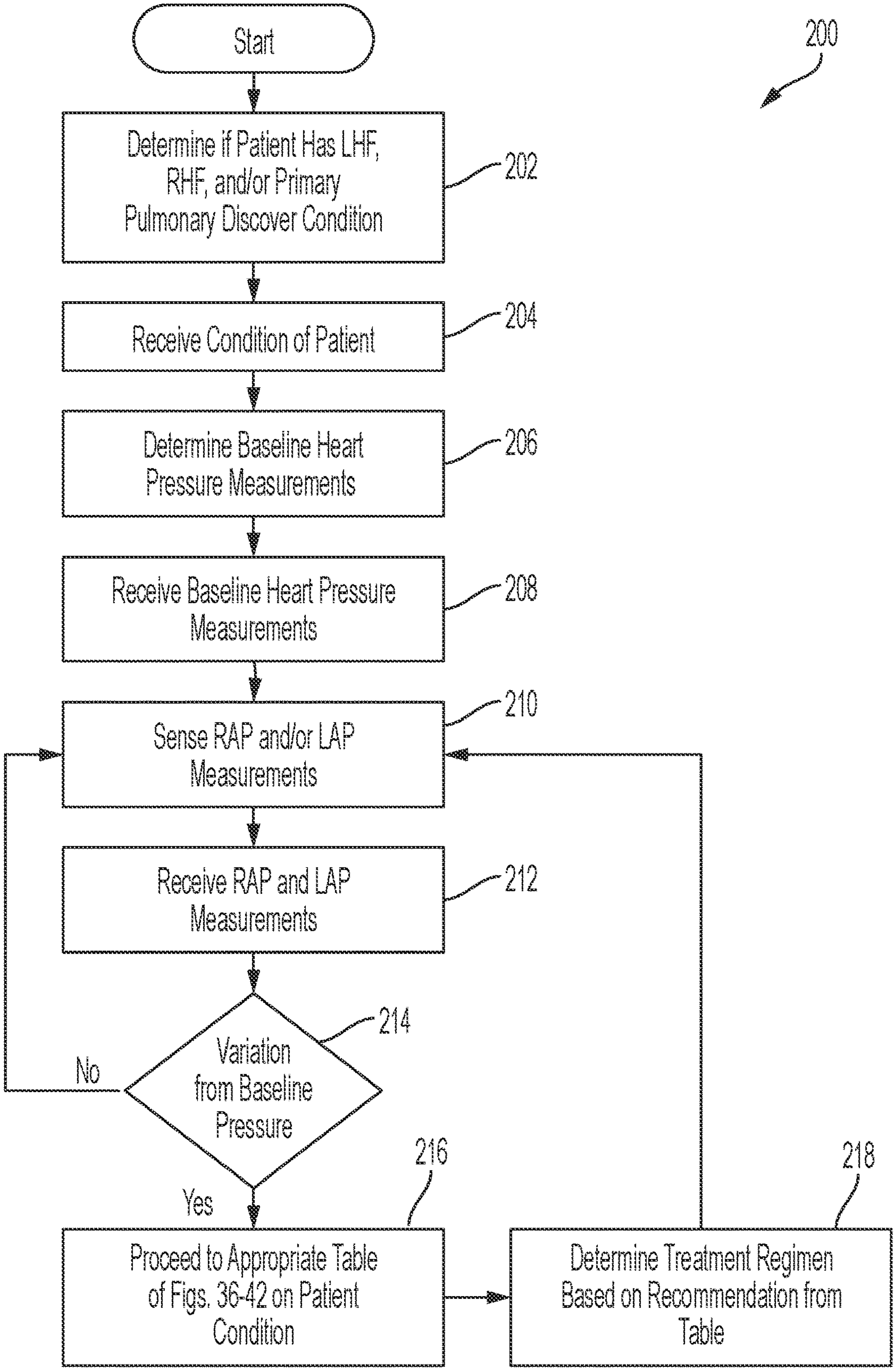
FIG. 10 illustrates a flow diagram of a method for determining a treatment regimen for a patient according to some embodiments.

FIG. 10 illustrates a flow diagram of a method 200 for determining a treatment regimen for a patient according to some embodiments. In at least some embodiments, the treatment regimen for the patient may include maintaining a dosing regimen for the patient, increasing the dosing regimen for the patient, decreasing the dosing regimen for the patient, changing the type of medication for the patient, confirming and/or checking the heart waveform for the patient, and/or suggesting the patient visit a medical professional for further testing and/or diagnosis. In at least some embodiments, the treatment regimen for the patient may be communicated to the patient by the monitoring system 62. In some embodiments, the embodiments described below for changing the type of medication for the patient may be determined by a processing device using machine learning techniques.

For example, the method 200 may be implemented using one or more electronic devices, such as the monitoring system 62, using measurement data received from, for example, the sensing device 61 or any of the sensor elements described herein. In at least some embodiments, the method 200 may be used for patients with a history of LHF, right heart failure (RHF), and/or primary pulmonary disorder to determine a treatment regimen guided by sensed left heart pressure measurements (e.g., left atrial pressure measurements) and/or right heart pressure measurements (e.g., right atrial pressure measurements).

In at least some embodiments, the method 200 (and/or algorithm 99) may be used in a closed loop system (e.g., diuretic and/or vasodilator pump) to reduce the need to rely on patient compliance. Additionally, or alternatively, the method 200 (and/or algorithm 99) may be used with and/or incorporated into a therapy device (e.g., VAD) to adjust device settings (e.g., VAD RPMs) in addition to medications.

In some embodiments, the method 200 includes determining if the patient has LHF, RHF, and/or primary pulmonary disorder condition (block 202). In at least some embodiments, a medical service professional may make the determination based on one or more of patient history, family history, a physical examination, chest radiography, electrocardiography, and/or the like. In embodiments, the method 200 may include inputting and/or communicating the condition of the patient to one or more devices (block 204). For example, the condition may be input into the monitoring system 62.

Some embodiments of the method 200 may also include determining one or more baseline heart pressure measurements (block 206). For example, in at least some embodiments, the baseline heart pressure measurements may be baseline left heart pressure measurements and/or baseline right heart pressure measurements. For example, the left heart pressure measurements may be left atrial pressure measurements (LAP) and the right heart pressure measurements may be right atrial pressure measurements (RAP). Additionally, or alternatively, other measurements may be sensed to represent the left heart and/or right heart pressures. For example, surrogates for the left heart pressure may be used as described above. As another example, surrogates for the right heart pressure may be used as described above.

In at least some embodiments, a Valsalva pressure measurement technique (remote or in office) may be used to re-calibrate the pressure sensing device 61 if the pressure reading is suspect to sensor drift. For example, the Valsalva airway pressure will equalize with RVEDP of the sensing device 61 and can be compared for recalibration.

In at least some embodiments, the baseline heart pressure measurements may be determined based on healthy heart pressure measurements. For example, a healthy heart may have left heart pressure measurements that are approximately $L_1$ and right heart pressure measurements that are approximately $R_1$. In embodiments, the baseline heart pressure measurements may be set to $L_1$ and $R_1$ +/− an appropriate variation. In at least some embodiments, the variation may be +/−10%, 20%, etc. As such, the baseline heart pressure measurements may be set to $L_1$ and $R_1$ +/−10%, 20%, etc.

Additionally, or alternatively, the baseline heart pressure measurements may be determined by a medical service provider based on the condition of the patient. For example, a medical service provider may assign baseline heart pressure measurements based on the condition of the patient (e.g., LHR, RHF, and/or primary pulmonary disorder) and/or may test the baseline heart pressure measurements of the patient in an acute setting by performing various tests on the patient to determine, based on the current condition of the patient, what normal heart pressure measurements would be. The baseline heart pressure measurements can then be input into and received by the monitoring system 62 (block 208).

The method 200 may also include sensing or determining the LAP and/or the RAP after baseline pressures are established (block 210). In at least some embodiments, the LAP and/or the RAP are sensed or determined at regular intervals. For example, the LAP and/or the RAP may be sensed every minute, every hour, every day, every week, every month, etc. As used throughout this description, either or both of LAP and RAP, including those used in connection with method 200 and/or algorithm 99, can be pressures determined by the methods described herein (e.g., by the use of sensing device 61 and monitoring system 62).

The method 200 may further include determining whether the sensed or determined LAP and/or the sensed or determined RAP vary from the baseline heart pressure measurements (block 214). For example, the monitoring system 62 may compare the LAP and/or the RAP sensed in block 210 with the baseline measurements established in block 208. The monitoring system 62 can then determine whether the LAP and/or RAP are below, at, or above the baseline heart pressure measurements established in block 208. For example, if the LAP and/or the RAP are within a threshold of the baseline heart pressure measurements, then the method 200 may proceed back to block 210 and continue to monitor the LAP and/or the RAP. Alternatively, if the LAP and/or the RAP are above or below the baseline heart pressure measurements by a threshold, then the method 200 may proceed to block 216.

In at least some embodiments, the threshold may be a percentage difference of the baseline heart pressure measurements. In some embodiments, the percentage difference may be input into the monitoring system 62. For example, the threshold may be +/−5%, +/−10%, +/−15%, +/−20%, +/−25%, etc. of the baseline heart pressure measurements. And, once a percentage threshold is selected and input into the monitoring system 62, if the sensed LAP and/or the sensed RAP are within the selected percentage of the baseline heart pressure measurements, then the method 200 may proceed to block 210. Alternatively, if the sensed LAP and/or the sensed RAP differ by the selected percentage or differ by more than the selected percentage from the baseline heart pressure measurements, then the method 200 may proceed to block 216.

In at least some other embodiments, the threshold may be a constant. In some embodiments, the percentage difference may be input into the monitoring system 62. For example, the threshold may be $x_1$ millimeters of mercury (mmHg). And, if the sensed LAP and/or the sensed RAP are within $x_1$ of the baseline heart pressure measurements, then the method 200 may proceed to block 210. Alternatively, if the sensed LAP and/or the sensed RAP differ by $x_1$ or differ by more than $x_1$ than the baseline heart pressure measurements, then the method 200 may proceed to block 216.

Additionally, or alternatively, the method 200 may also include determining a trend of the sensed LAP and/or the sensed RAP. For example, the monitoring system 62 may determine whether the pressure values are increasing, decreasing, or staying steady as an additional input into the overall assessment.

In the event the method 200 proceeds to block 216, the method 200 proceeds to appropriate figure of FIGS. 11-17, based on the patient's condition. That is, if the method 200 determines the patient has only LHF at block 202, then the method 200 proceeds to tables 300, 350 illustrated in FIG. 11. If the method 200 determines the patient has only RHF at block 202, then the method 200 proceeds to table 400, 450 illustrated in FIG. 12. If the method 200 determines the patient has only primary pulmonary disorder at block 202, then the method 200 proceeds to table 500, 550 illustrated in FIG. 13. If the method 200 determines the patient has only LHF and RHF at block 202, then the method 200 proceeds to table 600, 650 illustrated in FIG. 14. If the method 200 determines the patient has only LHF and primary pulmonary disorder at block 202, then the method 200 proceeds to table 700, 750 illustrated in FIG. 15. If the method 200 determines the patient has only RHF and primary pulmonary disorder at block 202, then the method 200 proceeds to table 800, 850 illustrated in FIG. 16. And, if the method 200 determines the patient has LHF, RHF, and primary pulmonary disorder at block 202, then the method 200 proceeds to table 900, 950 illustrated in FIG. 17. Once the appropriate table is referenced, the method 200 determines a treatment regimen for the patient based on the recommended treatment regimen from the table using the sensed LAP and/or the sensed RAP (block 218). In at least some embodiments, the monitoring system 62 may reference the appropriate table of the tables illustrated in FIGS. 11-17 and instruct (via a notification and/or other communication) the patient and/or medical professional to follow the treatment regimen proposed by the appropriate table. Once the treatment regimen is determined, administered, and/or communicated at block 218, the method 200 may return to block 210 to sense the LAP and/or RAP and continue through method 200 to determine whether the treatment regimen is effective. In at least some embodiments treatments may include, but are not limited to, diagnosis, medication titrations, advanced therapy, IV medications, lifestyle changes, intra-atrial shunts, valve repair/replace, ICDs, CRTs, and ablation. Exemplary medication titrations may include, but are not limited to, vasodilators, diuretics, pulmonary vasodilators, neurohormonal antagonists, beta blockers, and inotropes. Exemplary advanced therapies may include, but are not limited to, implanting a ventricular assist device (VAD), a transplant, or both. Exemplary lifestyle changes may include, but are not limited to, a change in diet, increased activity, or both.

The method 200 may be adjusted to be more specific in terms of how much a pharmacological, or medication regimen needs to be increased or reduced, which can be varied based on how much the LAP and RAP are above or below the baseline levels. This may be done by implementing another table or set of guidelines within the tables illustrated in FIGS. 1-17 that indicates the amount of medication to be administered (e.g., so that a treatment dosage regimen may be adjusted fora patient without requiring direct medical service provider intervention). Furthermore, to inform the patient on which medication to choose and its dosage, the type of medication (e.g. diuretic or vasodilator) that needs to be administered and the dosage thereof can be displayed on, for example, the screen of a computer or a display of a smart device used by the patient.

As explained above, the method 200 may be performed manually or may be partially or completely automated using any device capable of receiving and processing the measurement data from the sensing device 61. For example, the method 200 may be implemented entirely in the monitoring system 62 (e.g., such as a smart device), which performs all the comparisons, calculations, and determinations after receiving the LAP and RAP measurement data from the sensing device 61. In some examples, the method 200 may be implemented partially in the monitoring system 62 and partially in the communications relay 80 which may include a processing unit to receive the LAP and RAP measurement data from the sensors, determine whether the LAP and RAP are above/at/below normal level and decreasing/steady/increasing, then relay this information to the monitoring system 62 to perform the rest of the method. In yet another example, the sensing device 61 may be suitably structured and programmed to perform a portion or the entirety of the method 200.

In still further examples, the method 200 may be implemented in a device with a user interface allowing the patient to administer medications according to the results of the method 200. The method 200 may also be implemented in the medical service providers' electronic health record (EHR) or electronic medical record (EMR) systems which keep track of the necessary records of each patient. As such, the EHR or EMR systems may use local or remote database to access, among other things, the patient's history of LHF or RHF and whether the medical service providers have deemed the patient to be at a risk of such failure. The resulting data from the method 200 may be displayed on a dashboard of the user interface with multiple options for the user (e.g. patient and medical service providers), which may include: LAP and RAP averages, trend arrows, line graphs over time, and waveforms, as well as a history of the medications taken by the patient, etc. The dashboard may also be configured such that the user can first pull up the most meaningful information, such as the averages and trends, and a more detailed analysis can then be displayed, such as the waveforms. This may be implemented by organizing the multiple options in a hierarchical manner based on the importance of each option. In one example, this hierarchical order of the options is customizable according to the user's preference, such that the most preferred information can be pulled up first.

Figure 11:
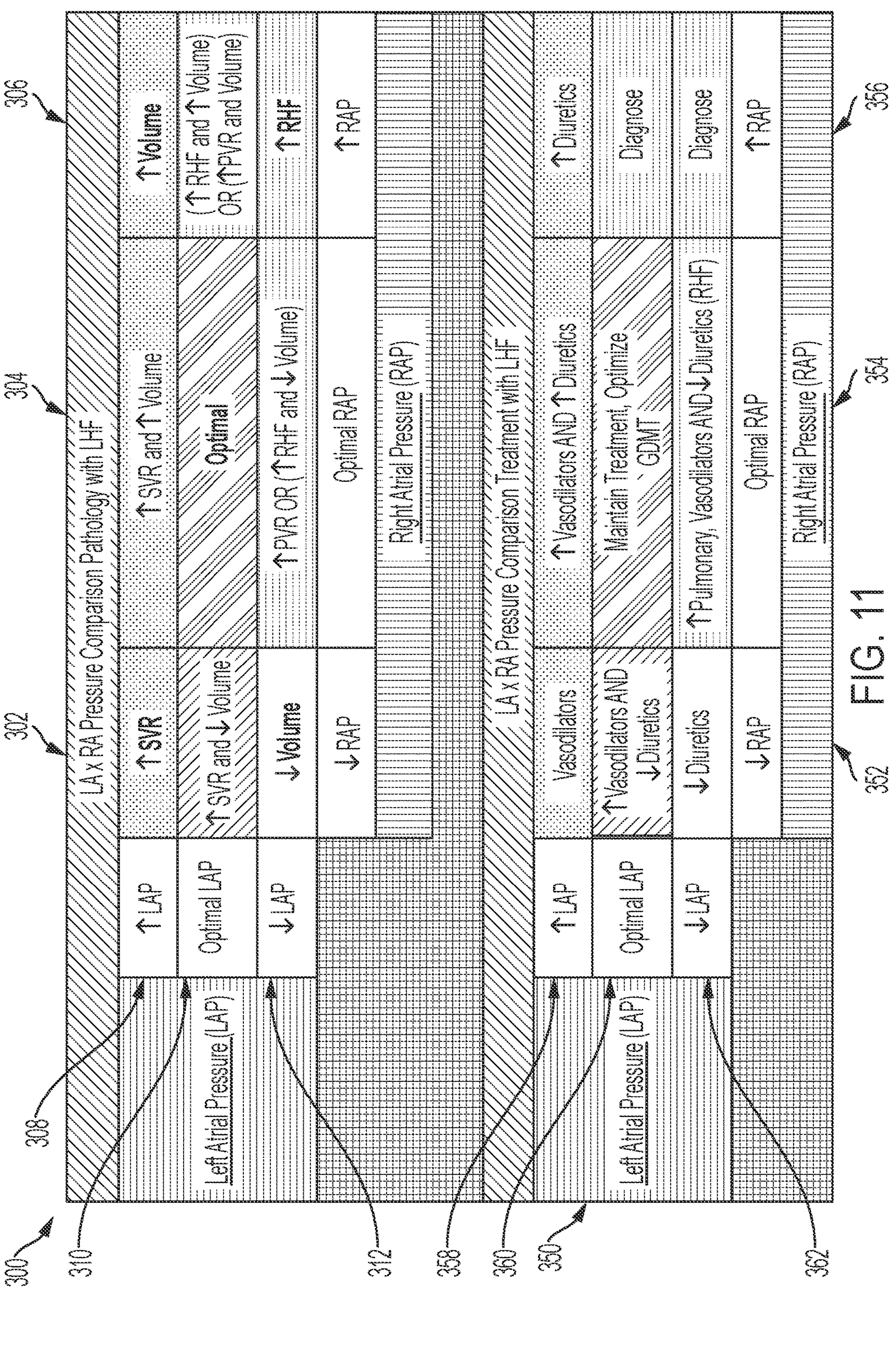
FIG. 11 illustrates an exemplary diagnostic table and an exemplary treatment regimen table referenced by the method in FIG. 10 fora patient diagnosed with left heart failure.

Referring to FIG. 11, an exemplary diagnostic regimen lookup table 300 and an exemplary treatment regimen lookup table 350 are illustrated fora patient diagnosed with the condition of LHF. In particular, the table 300 has three columns 302, 304, 306 and three rows 308, 310, 312 and each cell illustrates a pathology of the patient based on corresponding sensed heart pressure measurements for the patient. Similarly, the table 350 has three columns 352, 354, 356 and three rows 358, 360, 362 and each cell illustrates a treatment regimen for the patient based on corresponding sensed pressure measurements and the identified pathology in table 300. That is, columns 302, 352 pertain to the RAP sensed at block 210 (of FIG. 10) being lower than the baseline RAP determined at block 206 (of FIG. 10) by a threshold. Columns 304, 354 pertain to the RAP sensed at block 210 (of FIG. 10) being within a threshold of the baseline RAP determined at block 206 (of FIG. 10). Columns 306, 356 pertains to the RAP sensed at block 210 (of FIG. 10) being greater than the baseline RAP determined at block 206 (of FIG. 10) by a threshold. Rows 308, 358 pertain to the LAP sensed at block 210 (of FIG. 10) being higher than the baseline LAP determined at block 206 (of FIG. 10) by a threshold. Rows 310, 360 pertain to the LAP sensed at block 210 (of FIG. 10) being within a threshold of the baseline LAP determined at block 206 (of FIG. 10). And, rows 312, 362 pertain to the LAP sensed at block 210 (of FIG. 10) being less than the baseline LAP determined at block 206 (of FIG. 10) by a threshold.

Referring to columns 302, 352, the sensed RAP is lower than the baseline RAP by a threshold. In the event the sensed LAP is higher than the baseline LAP by a threshold, which corresponds to rows 308, 358, then it is likely the system is vascular resistance (SVR) of the patient has increased so the treatment regimen for the patient is to increase the vasodilator dosing regimen of the patient according to table 350. As another example and still referring to columns 302, 352, if the sensed LAP is within a threshold of the baseline LAP, which corresponds to rows 310, 360, then it is likely the SVR of the patient has increased and the intravascular volume of the patient has decreased, so the vasodilator dosing regimen of the patient is increased while the diuretic dosing regimen of the patient is decreased. As even another example and still referring to columns 302, 352, if the sensed LAP is lower than the baseline LAP by a threshold, which corresponds to rows 312, 362, then it is likely the intravascular volume of the patient has decreased, and the corresponding treatment regimen indicated in table 350 is to decrease the diuretic dosing regimen of the patient.

Referring to columns 304, 354, the sensed RAP is within a threshold of the baseline RAP. In the event the sensed LAP is higher than the baseline LAP by a threshold, then it is likely the SVR of the patient has increased and the intravascular volume of the patient has increased. In this case, the vasodilator dosing regimen of the patient is increased, and the diuretic dosing regimen of the patient is increased. As another example and still referring to columns 304, 354, if the sensed LAP is within a threshold of the baseline LAP, then it is likely the dosing regimen of the patient is effective, and the current treatment regimen is maintained. As even another example and still referring to columns 304, 354, if the sensed LAP is lower than the baseline LAP by a threshold, then it is likely the pulmonary vascular resistance (PVR) of the patient has increased, or the patient is experiencing RHF and the intravascular volume of the patient has decreased. In this case, the monitoring system 62 may suggest the patient visit a medical professional for further testing and/or diagnosis.

Referring to columns 306, 356, the sensed RAP is greater than the baseline RAP by a threshold. In the event the sensed LAP is higher than the baseline LAP by a threshold, then it is likely the intravascular volume of the patient has increased, so the diuretic dosing regimen of the patient is increased. As another example and still referring to columns 306, 356, if the sensed LAP is within a threshold of the baseline LAP, then the patient is likely experiencing RHF and increased intravascular volume, or the PVR of the patient has increased and the intravascular volume of the patient has increased. In this case, the monitoring system 62 may suggest the patient visit a medical professional for further testing and/or diagnosis. Additionally, or alternatively, the diagnosis may be performed automatically by the monitoring system 62. As even another example and still referring to columns 306, 356, if the sensed LAP is lower than the baseline LAP by a threshold, then it is likely the patient is experiencing RHF. In this case, the monitoring system 62 may suggest the patient visit a medical professional for further testing and/or diagnosis. Additionally, or alternatively, the diagnosis may be performed automatically by the monitoring system 62. For any of these dosing regimen changes, the monitoring system 62 may send a notification and/or send corresponding instructions to a therapy device.

Figure 12:
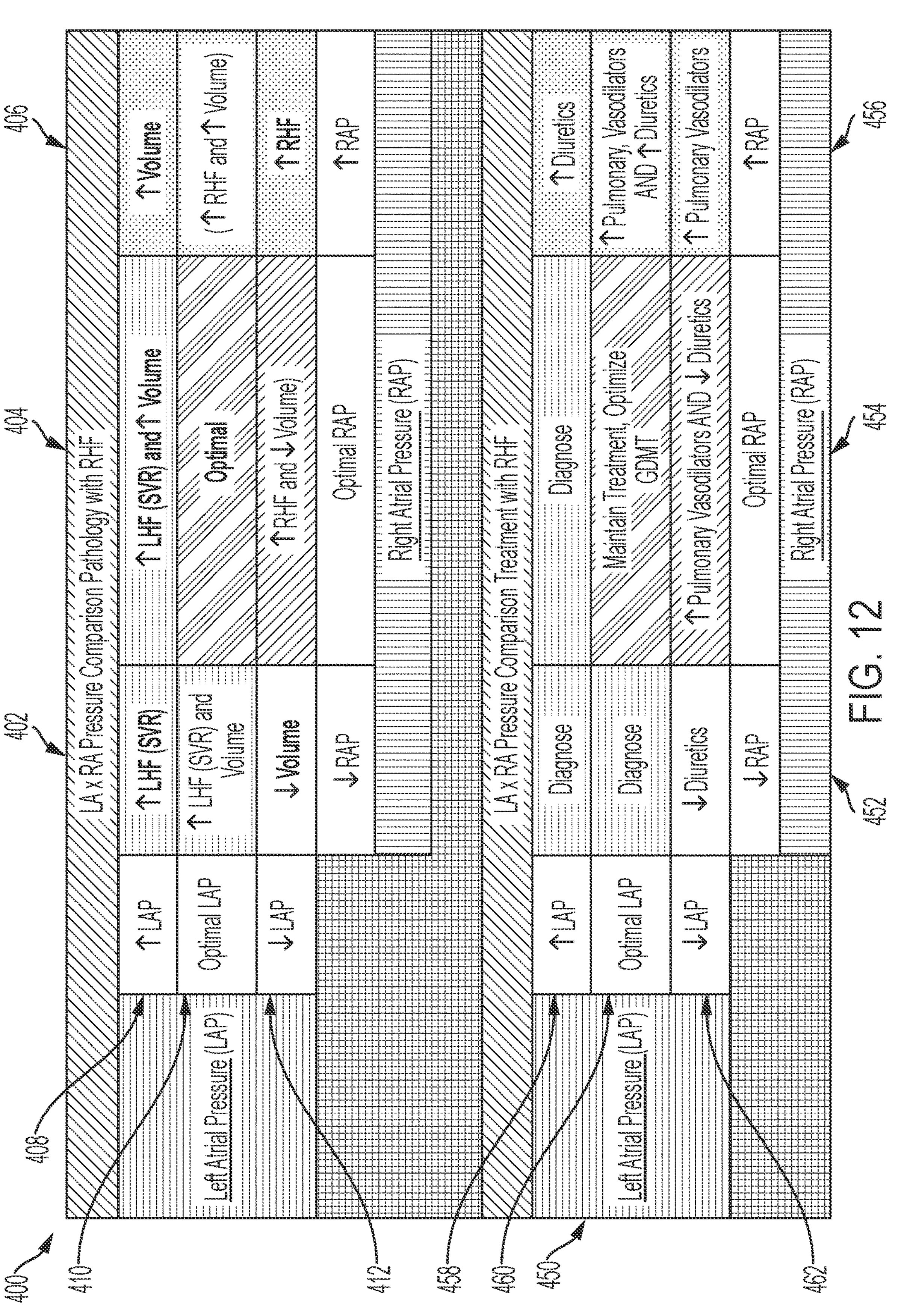
FIG. 12 illustrates an exemplary diagnostic table and an exemplary treatment regimen table referenced by the method in FIG. 10 fora patient diagnosed with right heart failure.

Referring to FIG. 12, an exemplary diagnostic regimen lookup table 400 and an exemplary treatment regimen lookup table 450 are illustrated fora patient diagnosed with the condition of RHF. In particular, the table 400 has three columns 402, 404, 406 and three rows 408, 410, 412 and each cell illustrates a pathology of the patient based on corresponding sensed heart pressure measurements for the patient. Similarly, the table 450 has three columns 452, 454, 456 and three rows 458, 460, 462 and each cell illustrates a treatment regimen for the patient based on corresponding sensed pressure measurements and the identified pathology in table 400. That is, columns 402, 452 pertain to the RAP sensed at block 210 (of FIG. 10) being lower than the baseline RAP determined at block 206 (of FIG. 10) by a threshold. Columns 404, 454 pertain to the RAP sensed at block 210 (of FIG. 10) being within a threshold of the baseline RAP determined at block 206 (of FIG. 10). Columns 406, 456 pertains to the RAP sensed at block 210 (of FIG. 10) being greater than the baseline RAP determined at block 206 (of FIG. 10) by a threshold. Rows 408, 458 pertain to the LAP sensed at block 210 (of FIG. 10) being higher than the baseline LAP determined at block 206 (of FIG. 10) by a threshold. Rows 410, 460 pertain to the LAP sensed at block 210 (of FIG. 10) being within a threshold of the baseline LAP determined at block 206 (of FIG. 10). And, rows 412, 462 pertain to the LAP sensed at block 210 (of FIG. 10) being less than the baseline LAP determined at block 206 (of FIG. 10) by a threshold.

Referring to columns 402, 452, the sensed RAP is lower than the baseline RAP by a threshold. In the event the sensed LAP is higher than the baseline LAP by a threshold, which corresponds to rows 408, 458, then it is likely the patient is experiencing LHF. In this case, the monitoring system 62 may suggest the patient visit a medical professional for further testing and/or diagnosis. Additionally, or alternatively, the diagnosis may be performed automatically by the monitoring system 62. As another example and still referring to columns 402, 452, if the sensed LAP is within a threshold of the baseline LAP, which corresponds to rows 410, 460, then it is likely the patient is experiencing LHF and the intravascular volume of the patient has decreased. In this case, the monitoring system 62 may suggest the patient visit a medical professional for further testing and/or diagnosis. Additionally, or alternatively, the diagnosis may be performed automatically by the monitoring system 62. As even another example and still referring to columns 402, 452, if the sensed LAP is lower than the baseline LAP by a threshold, which corresponds to rows 412, 462, then it is likely the intravascular volume of the patient has decreased, and the corresponding treatment regimen is to decrease the diuretic dosing regimen of the patient Referring to columns 404, 454, the sensed RAP is within a threshold of the baseline RAP. In the event the sensed LAP is higher than the baseline LAP by a threshold, then it is likely the patient is experiencing LHF and increased intravascular volume. In this case, the monitoring system 62 may suggest the patient visit a medical professional for further testing and/or diagnosis. Additionally, or alternatively, the diagnosis may be performed automatically by the monitoring system 62. As another example and still referring to columns 404, 454, if the sensed LAP is within a threshold of the baseline LAP, then it is likely the dosing regimen of the patient is effective, and the current treatment regimen is maintained. As even another example and still referring to columns 404, 454, if the sensed LAP is lower than the baseline LAP by a threshold, then it is likely the patient's RHF is getting worse and the intravascular volume of the patient has decreased. In this case, the corresponding treatment regimen is to increase the pulmonary vasodilators treatment regimen and decrease the diuretic treatment regimen.

Referring to columns 406, 456, the sensed RAP is greater than the baseline RAP by a threshold. In the event the sensed LAP is higher than the baseline LAP by a threshold, then it is likely the intravascular volume of the patient has increased so the corresponding treatment regimen indicated in table 450 is to increase the diuretic dosing regimen of the patient. As another example and still referring to columns 406, 456, if the sensed LAP is within a threshold of the baseline LAP, then the patient's RHF is likely worsening and the intravascular volume of the patient has increased. In this case, the corresponding dosing regimen indicated in table 450 is to increase pulmonary vasodilators and increase diuretics. As even another example and still referring to columns 406, 456, if the sensed LAP is lower than the baseline LAP by a threshold, then it is likely the patient's RHF is worsening. In this case, the corresponding treatment regimen indicated in table 450 is to increase the pulmonary vasodilators. For any of these dosing regimen changes, the monitoring system 62 may send a notification and/or send corresponding instructions to a therapy device.

Figure 13:
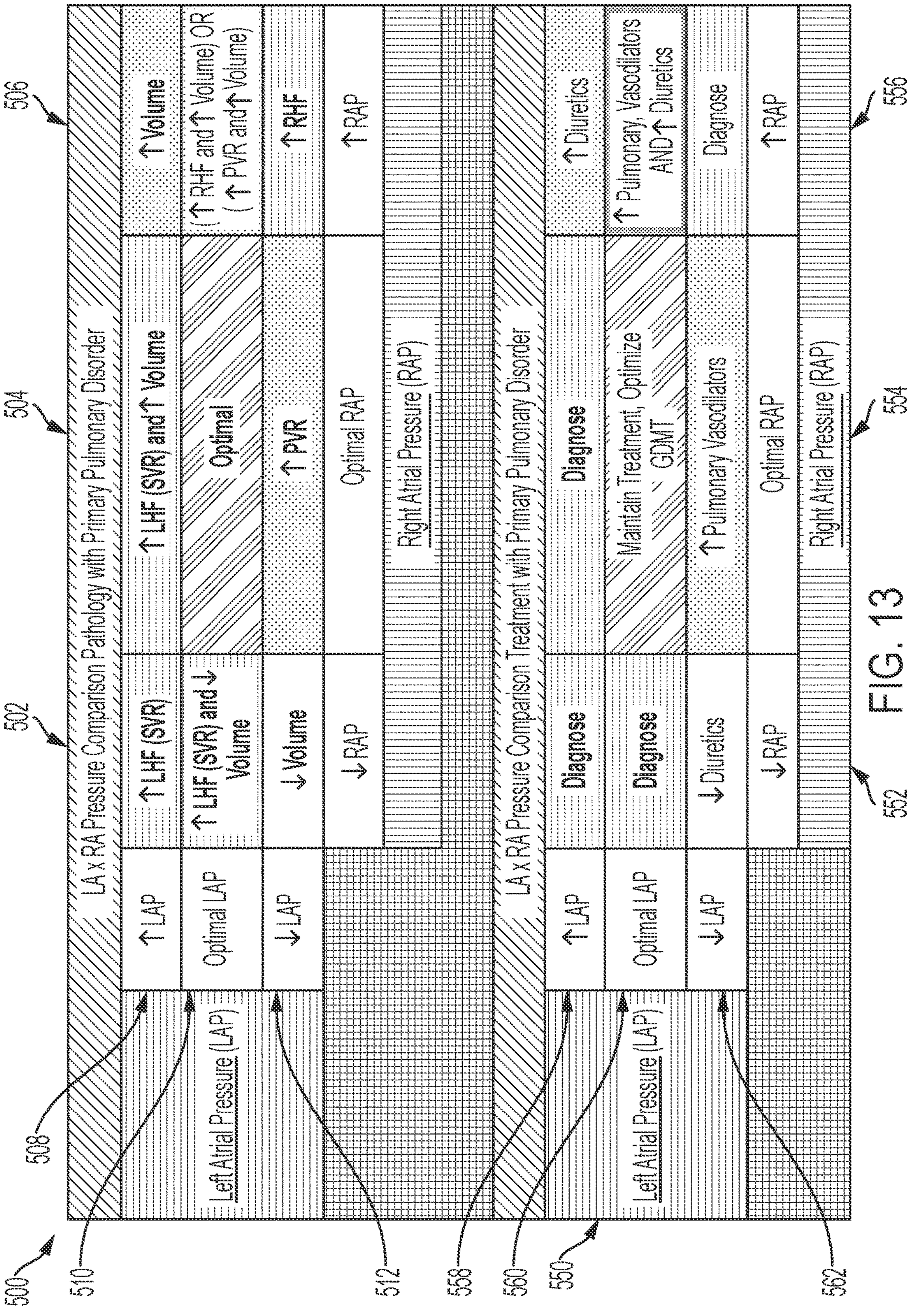
FIG. 13 illustrates an exemplary diagnostic table and an exemplary treatment regimen table referenced by the method in FIG. 10 fora patient diagnosed with primary pulmonary disorder.

Referring to FIG. 13, an exemplary diagnostic regimen lookup table 500 and an exemplary treatment regimen lookup table 550 are illustrated fora patient diagnosed with the condition of primary pulmonary disorder. In particular, the table 500 has three columns 502, 504, 506 and three rows 508, 510, 512 and each cell illustrates a pathology of the patient based on corresponding sensed heart pressure measurements for the patient. Similarly, the table 550 has three columns 552, 554, 556 and three rows 558, 560, 562 and each cell illustrates a treatment regimen for the patient based on corresponding sensed pressure measurements and the identified pathology in Table 500. That is, columns 502, 552 pertain to the RAP sensed at block 210 (of FIG. 10) being lower than the baseline RAP determined at block 206 (of FIG. 10) by a threshold. Columns 504, 554 pertain to the RAP sensed at block 210 (of FIG. 10) being within a threshold of the baseline RAP determined at block 206 (of FIG. 10). Columns 506, 556 pertains to the RAP sensed at block 210 (of FIG. 10) being greater than the baseline RAP determined at block 206 (of FIG. 10) by a threshold. Rows 508, 558 pertain to the LAP sensed at block 210 (of FIG. 10) being higher than the baseline LAP determined at block 206 (of FIG. 10) by a threshold. Rows 510, 560 pertain to the LAP sensed at block 210 (of FIG. 10) being within a threshold of the baseline LAP determined at block 206 (of FIG. 10). And, rows 512, 562 pertain to the LAP sensed at block 210 (of FIG. 10) being less than the baseline LAP determined at block 206 (of FIG. 10) by a threshold.

Referring to columns 502, 552, the sensed RAP is lower than the baseline RAP by a threshold. In the event the sensed LAP is higher than the baseline LAP by a threshold, which corresponds to rows 508, 558, then it is likely the patient is experiencing LHF. In this case, the monitoring system 62 may suggest the patient visit a medical professional for further testing and/or diagnosis. Additionally, or alternatively, the diagnosis may be performed automatically by the monitoring system 62. As another example and still referring to columns 502, 552, if the sensed LAP is within a threshold of the baseline LAP, which corresponds to rows 510, 560, then it is likely the patient is experiencing LHF and the intravascular volume of the patient has decreased. In this case, the monitoring system 62 may suggest the patient visit a medical professional for further testing and/or diagnosis. Additionally, or alternatively, the diagnosis may be performed automatically by the monitoring system 62. As even another example and still referring to columns 502, 552, if the sensed LAP is lower than the baseline LAP by a threshold, which corresponds to rows 512, 562, then it is likely the intravascular volume of the patient has decreased, and the corresponding treatment regimen is to decrease the diuretic dosing regimen of the patient.

Referring to columns 504, 554, the sensed RAP is within a threshold of the baseline RAP. In the event the sensed LAP is higher than the baseline LAP by a threshold, then it is likely the patient is experiencing LHF and increased intravascular volume. In this case, the monitoring system 62 may suggest the patient visit a medical professional for further testing and/or diagnosis. Additionally, or alternatively, the diagnosis may be performed automatically by the monitoring system 62. As another example and still referring to columns 504, 554, if the sensed LAP is within a threshold of the baseline LAP, then it is likely the dosing regimen of the patient is effective, and the current treatment regimen is maintained. As even another example and still referring to columns 504, 554, if the sensed LAP is lower than the baseline LAP by a threshold, then it is likely the patient's PVR is worsening. In this case, the corresponding treatment regimen is to increase the pulmonary vasodilators treatment regimen.

Referring to columns 506, 556, the sensed RAP is greater than the baseline RAP by a threshold. In the event the sensed LAP is higher than the baseline LAP by a threshold, then it is likely the intravascular volume of the patient has increased so the corresponding treatment regimen indicated in table 550 is to increase the diuretic dosing regimen of the patient. As another example and still referring to columns 506, 556, if the sensed LAP is within a threshold of the baseline LAP, then the patient is experiencing RHF and the intravascular volume of the patient has increased, or the patients PVR is worsening and the intravascular volume of the patient has increased. In this case, the corresponding dosing regimen indicated in table 550 is to increase pulmonary vasodilators and increase diuretics. As even another example and still referring to columns 506, 556, if the sensed LAP is lower than the baseline LAP by a threshold, then it is likely the patient is experiencing RHF. In this case, the monitoring system 62 may suggest the patient visit a medical professional for further testing and/or diagnosis. Additionally, or alternatively, the diagnosis may be performed automatically by the monitoring system 62. For any of these dosing regimen changes, the monitoring system 62 may send a notification and/or send corresponding instructions to a therapy device.

Figure 14:
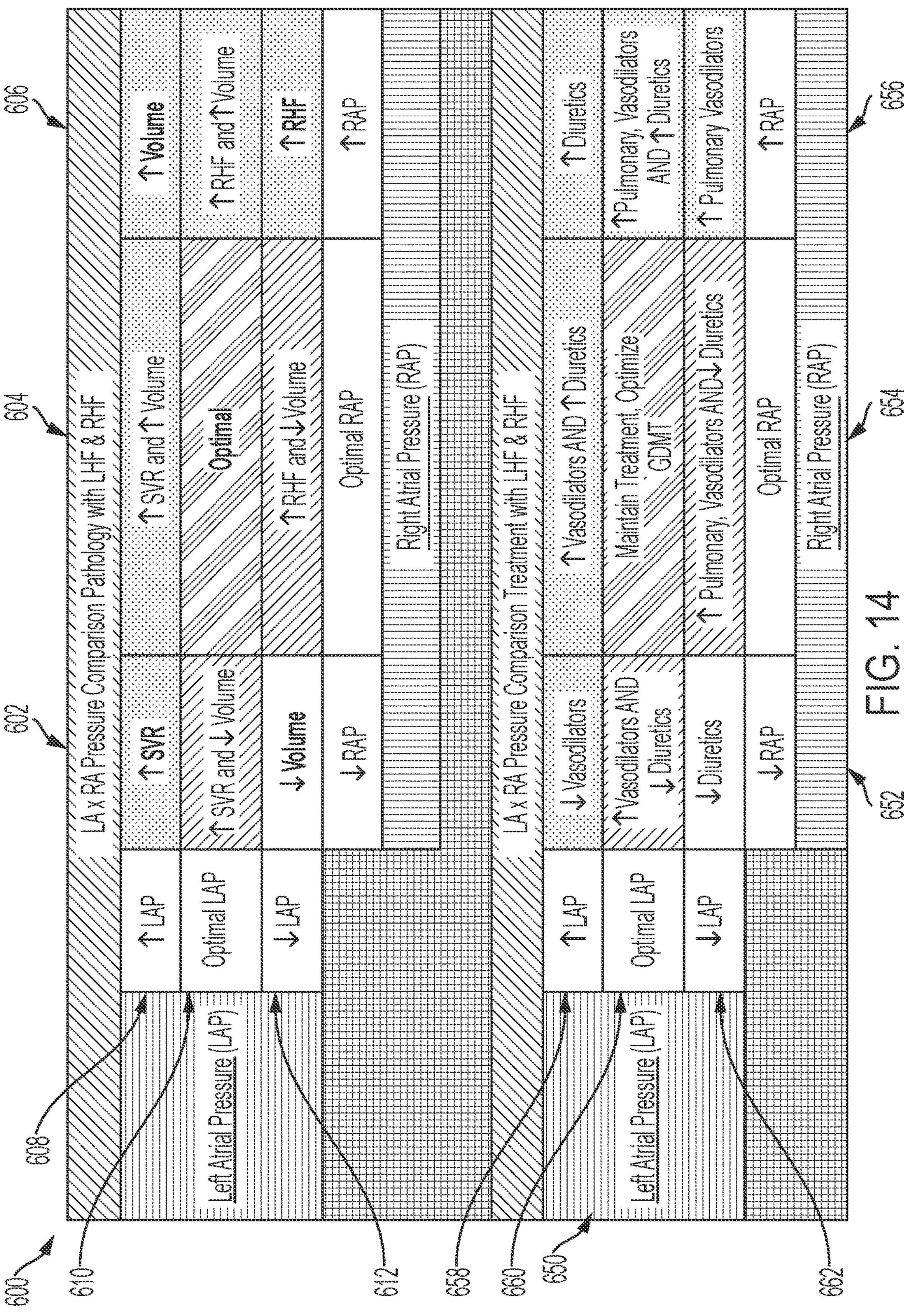
FIG. 14 illustrates an exemplary diagnostic table and an exemplary treatment regimen table referenced by the method in FIG. 10 fora patient diagnosed with left heart failure and right heart failure.

Referring to FIG. 14, an exemplary diagnostic regimen lookup table 600 and an exemplary treatment regimen lookup table 650 are illustrated for a patient diagnosed with the condition of LHF and RHF. In particular, the table 600 has three columns 602, 604, 606 and three rows 608, 610, 612 and each cell illustrates a pathology of the patient based on corresponding sensed heart pressure measurements for the patient. Similarly, the table 650 has three columns 652, 654, 656 and three rows 658, 660, 662 and each cell illustrates a treatment regimen for the patient based on corresponding sensed pressure measurements and the identified pathology in Table 600. That is, columns 602, 652 pertain to the RAP sensed at block 210 (of FIG. 10) being lower than the baseline RAP determined at block 206 (of FIG. 10) by a threshold. Columns 604, 654 pertain to the RAP sensed at block 210 (of FIG. 10) being within a threshold of the baseline RAP determined at block 206 (of FIG. 10). Columns 606, 656 pertains to the RAP sensed at block 210 (of FIG. 10) being greater than the baseline RAP determined at block 206 (of FIG. 10) by a threshold. Rows 608, 658 pertain to the LAP sensed at block 210 (of FIG. 10) being higher than the baseline LAP determined at block 206 (of FIG. 10) by a threshold. Rows 610, 660 pertain to the LAP sensed at block 210 (of FIG. 10) being within a threshold of the baseline LAP determined at block 206 (of FIG. 10). And, rows 612, 662 pertain to the LAP sensed at block 210 (of FIG. 10) being less than the baseline LAP determined at block 206 (of FIG. 10) by a threshold.

Referring to columns 602, 652, the sensed RAP is lower than the baseline RAP by a threshold. In the event the sensed LAP is higher than the baseline LAP by a threshold, which corresponds to rows 608, 658, then it is likely the SVR of the patient has increased so the treatment regimen for the patient is to increase the vasodilator dosing regimen of the patient, as indicated in table 650. As another example and still referring to columns 602, 652, if the sensed LAP is within a threshold of the baseline LAP, which corresponds to rows 610, 660, then it is likely the SVR of the patient has increased and the intravascular volume of the patient has decreased, so the corresponding treatment regimen indicated in table 650 is to increase the vasodilator dosing regimen of the patient while decreasing the diuretic dosing regimen of the patient. As even another example and still referring to columns 602, 652, if the sensed LAP is lower than the baseline LAP by a threshold, which corresponds to rows 612, 662, then it is likely the intravascular volume of the patient has decreased, and the corresponding treatment regimen indicated in table 650 is to decrease the diuretic dosing regimen of the patient.

Referring to columns 604, 654, the sensed RAP is within a threshold of the baseline RAP. In the event the sensed LAP is higher than the baseline LAP by a threshold, then it is likely the SVR of the patient has increased and the intravascular volume of the patient has increased. In this case, the vasodilator dosing regimen of the patient is increased, and the diuretic dosing regimen of the patient is increased. As another example and still referring to columns 604, 654, if the sensed LAP is within a threshold of the baseline LAP, then it is likely the dosing regimen of the patient is effective, and the current treatment regimen is maintained. As even another example and still referring to columns 604, 654, if the sensed LAP is lower than the baseline LAP by a threshold, then it is likely the patient's RHF is worsening and the intravascular volume of the patient has decreased. In this case, the treatment regimen indicated in table 650 is to increase the pulmonary vasodilators dosing regimen and decrease the diuretic dosing regimen.

Referring to columns 606, 656, the sensed RAP is greater than the baseline RAP by a threshold. In the event the sensed LAP is higher than the baseline LAP by a threshold, then it is likely the intravascular volume of the patient has increased so the corresponding treatment regimen indicated in table 650 is to increase the diuretic dosing regimen of the patient. As another example and still referring to columns 606, 656, if the sensed LAP is within a threshold of the baseline LAP, then the patient's RHF is likely worsening and the intravascular volume of the patient has increased. In this case, the corresponding dosing regimen indicated in table 650 is to increase pulmonary vasodilators and increase diuretics. As even another example and still referring to columns 606, 656, if the sensed LAP is lower than the baseline LAP by a threshold, then it is likely the patient's RHF is worsening. In this case, the corresponding treatment regimen indicated in table 650 is to increase the pulmonary vasodilators. For any of these dosing regimen changes, the monitoring system 62 may send a notification and/or send corresponding instructions to a therapy device.

Figure 15:
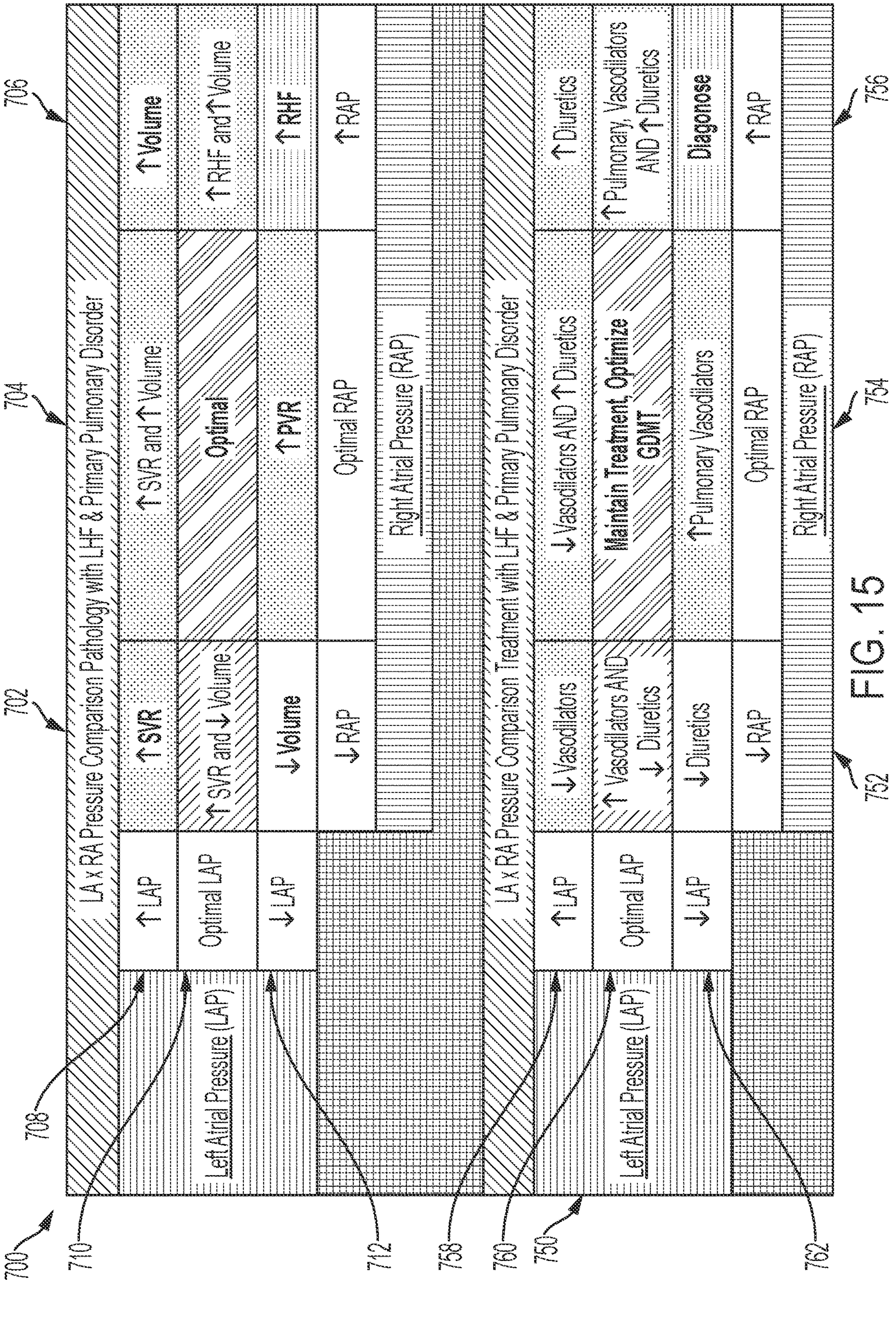
FIG. 15 illustrates an exemplary diagnostic table and an exemplary treatment regimen table referenced by the method in FIG. 10 fora patient diagnosed with left heart failure and primary pulmonary disorder.

Referring to FIG. 15, an exemplary diagnostic regimen lookup table 700 and an exemplary treatment regimen lookup table 750 are illustrated fora patient diagnosed with the condition of LHF and primary pulmonary disorder. In particular, the table 700 has three columns 702, 704, 706 and three rows 708, 710, 712 and each cell illustrates a pathology of the patient based on corresponding sensed heart pressure measurements for the patient. Similarly, the table 750 has three columns 752, 754, 756 and three rows 758, 760, 762 and each cell illustrates a treatment regimen for the patient based on corresponding sensed pressure measurements and the identified pathology in Table 700. That is, columns 702, 752 pertain to the RAP sensed at block 210 (of FIG. 10) being lower than the baseline RAP determined at block 206 (of FIG. 10) by a threshold. Columns 704, 754 pertain to the RAP sensed at block 210 (of FIG. 10) being within a threshold of the baseline RAP determined at block 206 (of FIG. 10). Columns 706, 756 pertains to the RAP sensed at block 210 (of FIG. 10) being greater than the baseline RAP determined at block 206 (of FIG. 10) by a threshold. Rows 708, 758 pertain to the LAP sensed at block 210 (of FIG. 10) being higher than the baseline LAP determined at block 206 (of FIG. 10) by a threshold. Rows 710, 760 pertain to the LAP sensed at block 210 (of FIG. 10) being within a threshold of the baseline LAP determined at block 206 (of FIG. 10). And, rows 712, 762 pertain to the LAP sensed at block 210 (of FIG. 10) being less than the baseline LAP determined at block 206 (of FIG. 10) by a threshold.

Referring to columns 702, 752, the sensed RAP is lower than the baseline RAP by a threshold. In the event the sensed LAP is higher than the baseline LAP by a threshold, which corresponds to rows 708, 758, then it is likely the SVR of the patient has increased so the treatment regimen for the patient is to increase the vasodilator dosing regimen of the patient, as indicated in table 750. As another example and still referring to columns 702, 752, if the sensed LAP is within a threshold of the baseline LAP, which corresponds to rows 710, 760, then it is likely the SVR of the patient has increased and the intravascular volume of the patient has decreased, so the corresponding treatment regimen indicated in table 750 is to increase the vasodilator dosing regimen of the patient while decreasing the diuretic dosing regimen of the patient. As even another example and still referring to columns 702, 752, if the sensed LAP is lower than the baseline LAP by a threshold, which corresponds to rows 712, 762, then it is likely the intravascular volume of the patient has decreased, and the corresponding treatment regimen indicated in table 750 is to decrease the diuretic dosing regimen of the patient.

Referring to columns 704, 754, the sensed RAP is within a threshold of the baseline RAP. In the event the sensed LAP is higher than the baseline LAP by a threshold, then it is likely the SVR of the patient has increased and the intravascular volume of the patient has increased. In this case, the corresponding treatment regimen indicated in table 750 is to increase the vasodilator dosing regimen for the patient and increase the diuretic dosing regimen of the patient. As another example and still referring to columns 704, 754, if the sensed LAP is within a threshold of the baseline LAP, then it is likely the dosing regimen of the patient is effective, and the current treatment regimen is maintained. As even another example and still referring to columns 704, 754, if the sensed LAP is lower than the baseline LAP by a threshold, then it is likely the patient's PVR is worsening. In this case, the treatment regimen indicated in table 750 is to increase the pulmonary vasodilators dosing regimen for the patient.

Referring to columns 706, 756, the sensed RAP is greater than the baseline RAP by a threshold. In the event the sensed LAP is higher than the baseline LAP by a threshold, then it is likely the intravascular volume of the patient has increased so the corresponding treatment regimen indicated in table 750 is to increase the diuretic dosing regimen of the patient. As another example and still referring to columns 706, 756, if the sensed LAP is within a threshold of the baseline LAP, then the patient's PVR is likely worsening and the intravascular volume of the patient has increased. In this case, the corresponding dosing regimen indicated in table 750 is to increase pulmonary vasodilators and increase diuretics. As even another example and still referring to columns 706, 756, if the sensed LAP is lower than the baseline LAP by a threshold, then it is likely the patient is experiencing RHF. In this case, the monitoring system 62 may suggest the patient visit a medical professional for further testing and/or diagnosis. Additionally, or alternatively, the diagnosis may be performed automatically by the monitoring system 62. For any of these dosing regimen changes, the monitoring system 62 may send a notification and/or send corresponding instructions to a therapy device.

Figure 16:
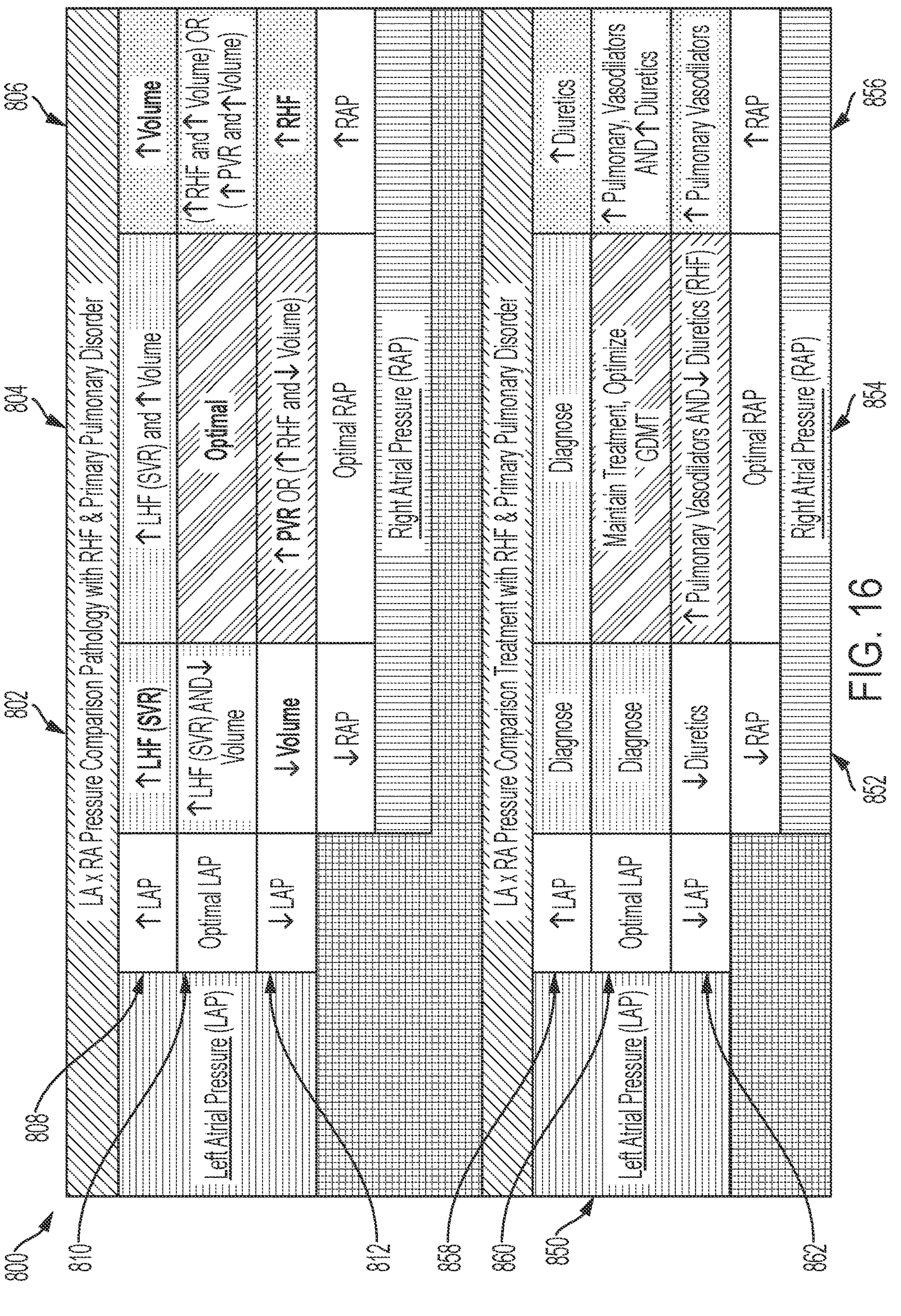
FIG. 16 illustrates an exemplary diagnostic table and an exemplary treatment regimen table referenced by the method in FIG. 10 fora patient diagnosed with right heart failure and primary pulmonary disorder.

Referring to FIG. 16, an exemplary diagnostic regimen lookup table 800 and an exemplary treatment regimen lookup table 850 are illustrated fora patient diagnosed with the condition of RHF and primary pulmonary disorder. In particular, the table 800 has three columns 802, 804, 806 and three rows 808, 810, 812 and each cell illustrates a pathology of the patient based on corresponding sensed heart pressure measurements for the patient. Similarly, the table 850 has three columns 852, 854, 856 and three rows 858, 860, 862 and each cell illustrates a treatment regimen for the patient based on corresponding sensed pressure measurements and the identified pathology in Table 800. That is, columns 802, 852 pertain to the RAP sensed at block 210 (of FIG. 10) being lower than the baseline RAP determined at block 206 (of FIG. 10) by a threshold. Columns 804, 854 pertain to the RAP sensed at block 210 (of FIG. 10) being within a threshold of the baseline RAP determined at block 206 (of FIG. 10). Columns 806, 856 pertains to the RAP sensed at block 210 (of FIG. 10) being greater than the baseline RAP determined at block 206 (of FIG. 10) by a threshold. Rows 808, 858 pertain to the LAP sensed at block 210 (of FIG. 10) being higher than the baseline LAP determined at block 206 (of FIG. 10) by a threshold. Rows 810, 860 pertain to the LAP sensed at block 210 (of FIG. 10) being within a threshold of the baseline LAP determined at block 206 (of FIG. 10). And, rows 812, 862 pertain to the LAP sensed at block 210 (of FIG. 10) being less than the baseline LAP determined at block 206 (of FIG. 10) by a threshold.

Referring to columns 802, 852, the sensed RAP is lower than the baseline RAP by a threshold. In the event the sensed LAP is higher than the baseline LAP by a threshold, which corresponds to rows 808, 858, then it is likely the patient is experiencing LHF. In this case, the monitoring system 62 may suggest the patient visit a medical professional for further testing and/or diagnosis. Additionally, or alternatively, the diagnosis may be performed automatically by the monitoring system 62. As another example and still referring to columns 802, 852, if the sensed LAP is within a threshold of the baseline LAP, which corresponds to rows 810, 860, then it is likely the patient is experiencing LHF and the intravascular volume of the patient has decreased. In this case, the monitoring system 62 may suggest the patient visit a medical professional for further testing and/or diagnosis. Additionally, or alternatively, the diagnosis may be performed automatically by the monitoring system 62. As even another example and still referring to columns 802, 852, if the sensed LAP is lower than the baseline LAP by a threshold, which corresponds to rows 812, 862, then it is likely the intravascular volume of the patient has decreased, and the corresponding treatment regimen is to decrease the diuretic dosing regimen of the patient.

Referring to columns 804, 854, the sensed RAP is within a threshold of the baseline RAP. In the event the sensed LAP is higher than the baseline LAP by a threshold, then it is likely the patient is experiencing LHF and increased intravascular volume. In this case, the monitoring system 62 may suggest the patient visit a medical professional for further testing and/or diagnosis. Additionally, or alternatively, the diagnosis may be performed automatically by the monitoring system 62. As another example and still referring to columns 804, 854, if the sensed LAP is within a threshold of the baseline LAP, then it is likely the dosing regimen of the patient is effective, and the current treatment regimen is maintained. As even another example and still referring to columns 804, 854, if the sensed LAP is lower than the baseline LAP by a threshold, then it is likely the patient's PVR is worsening or the patient's RHF is worsening and the intravascular volume of the patient has increased. In this case, the corresponding treatment regimen illustrated in table 850 is to increase the pulmonary vasodilators treatment regimen and decrease the diuretic treatment regimen for the patient.

Referring to columns 806, 856, the sensed RAP is greater than the baseline RAP by a threshold. In the event the sensed LAP is higher than the baseline LAP by a threshold, then it is likely the intravascular volume of the patient has increased so the corresponding treatment regimen indicated in table 850 is to increase the diuretic dosing regimen of the patient. As another example and still referring to columns 806, 856, if the sensed LAP is within a threshold of the baseline LAP, then the patient's RHF is likely worsening and the intravascular volume of the patient has increased or the patient's PVR is worsening and the intravascular volume of the patient has increased. In this case, the corresponding dosing regimen indicated in table 850 is to increase pulmonary vasodilators and increase diuretics. As even another example and still referring to columns 806, 856, if the sensed LAP is lower than the baseline LAP by a threshold, then it is likely the patient's RHF is worsening. In this case, the corresponding treatment regimen indicated in table 850 is to increase the pulmonary vasodilators. For any of these dosing regimen changes, the monitoring system 62 may send a notification and/or send corresponding instructions to a therapy device.

Figure 17:
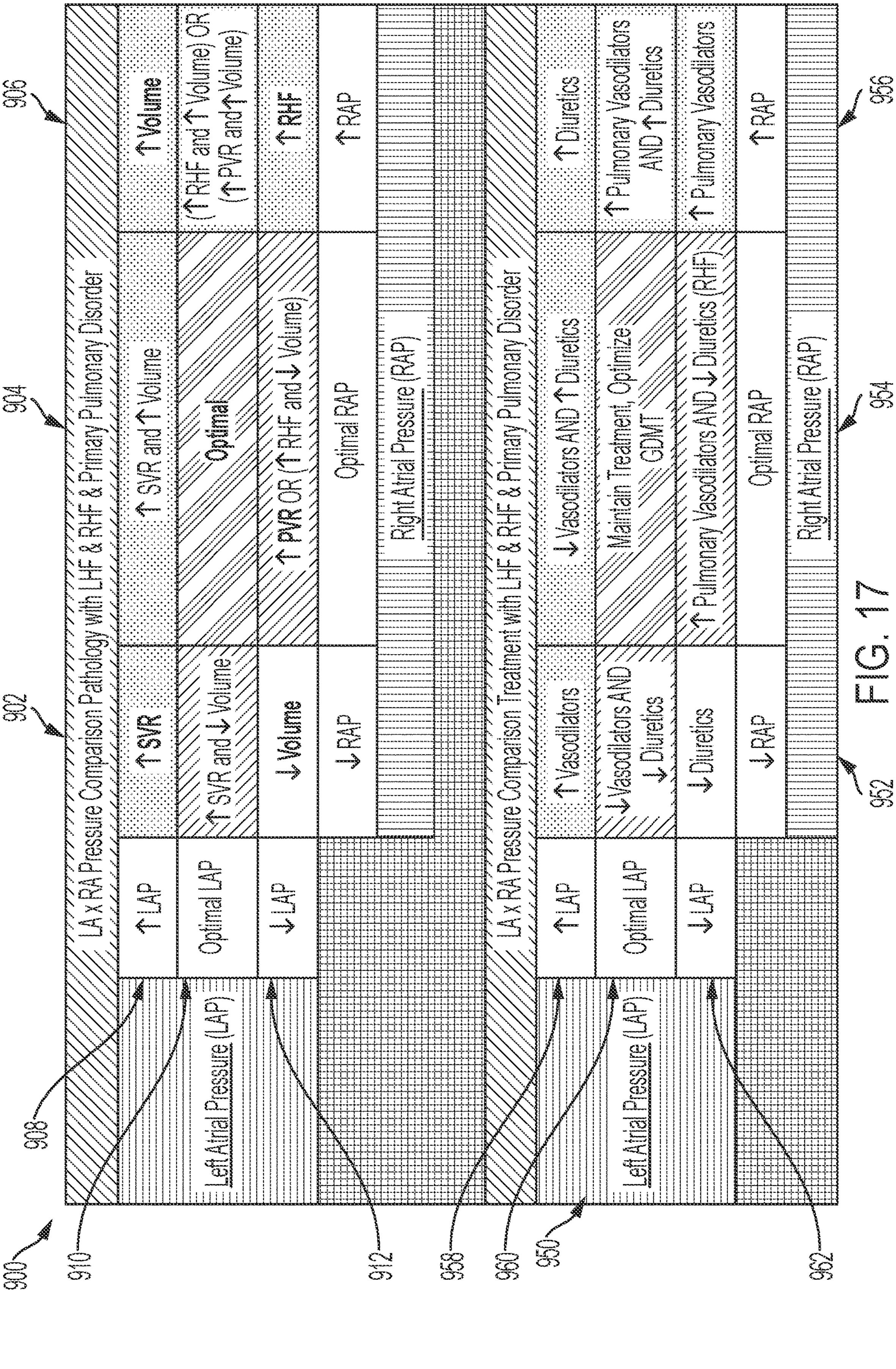
FIG. 17 illustrates an exemplary diagnostic table and an exemplary treatment regimen table referenced by the method in FIG. 10 fora patient diagnosed with left heart failure, right heart failure, and primary pulmonary disorder.

Referring to FIG. 17, an exemplary diagnostic regimen lookup table 900 and an exemplary treatment regimen lookup table 950 for a patient diagnosed with the condition of LHF, RHF, and primary pulmonary disorder are illustrated. In particular, the table 900 has three columns 902, 904, 906 and three rows 908, 910, 912 and each cell illustrates a pathology of the patient based on corresponding sensed heart pressure measurements for the patient. Similarly, the table 950 has three columns 952, 954, 956 and three rows 958, 960, 962 and each cell illustrates a treatment regimen for the patient based on corresponding sensed pressure measurements and the identified pathology in Table 900. That is, columns 902, 952 pertain to the RAP sensed at block 210 (of FIG. 10) being lower than the baseline RAP determined at block 206 (of FIG. 10) by a threshold. Columns 904, 954 pertain to the RAP sensed at block 210 (of FIG. 10) being within a threshold of the baseline RAP determined at block 206 (of FIG. 10). Columns 906, 956 pertains to the RAP sensed at block 210 (of FIG. 10) being greater than the baseline RAP determined at block 206 (of FIG. 10) by a threshold. Rows 908, 958 pertain to the LAP sensed at block 210 (of FIG. 10) being higher than the baseline LAP determined at block 206 (of FIG. 10) by a threshold. Rows 910, 960 pertain to the LAP sensed at block 210 (of FIG. 10) being within a threshold of the baseline LAP determined at block 206 (of FIG. 10). And, rows 912, 962 pertain to the LAP sensed at block 210 (of FIG. 10) being less than the baseline LAP determined at block 206 (of FIG. 10) by a threshold.

Referring to columns 902, 952, the sensed RAP is lower than the baseline RAP by a threshold. In the event the sensed LAP is higher than the baseline LAP by a threshold, which corresponds to rows 908, 958, then it is likely the SVR of the patient has increased so the treatment regimen for the patient is to increase the vasodilator dosing regimen of the patient, as indicated in table 950. As another example and still referring to columns 902, 952, if the sensed LAP is within a threshold of the baseline LAP, which corresponds to rows 910, 960, then it is likely the SVR of the patient has increased and the intravascular volume of the patient has decreased, so the corresponding treatment regimen indicated in table 950 is to increase the vasodilator dosing regimen of the patient while decreasing the diuretic dosing regimen of the patient. As even another example and still referring to columns 902, 952, if the sensed LAP is lower than the baseline LAP by a threshold, which corresponds to rows 912, 962, then it is likely the intravascular volume of the patient has decreased, and the corresponding treatment regimen indicated in table 950 is to decrease the diuretic dosing regimen of the patient.

Referring to columns 904, 954, the sensed RAP is within a threshold of the baseline RAP. In the event the sensed LAP is higher than the baseline LAP by a threshold, then it is likely the SVR of the patient has increased and the intravascular volume of the patient has increased. In this case, the vasodilator dosing regimen of the patient is increased, and the diuretic dosing regimen of the patient is increased. As another example and still referring to columns 904, 954, if the sensed LAP is within a threshold of the baseline LAP, then it is likely the dosing regimen of the patient is effective, and the current treatment regimen is maintained. As even another example and still referring to columns 904, 954, if the sensed LAP is lower than the baseline LAP by a threshold, then it is likely the patient's PVR has increased, or the patient's RHF is worsening and the intravascular volume of the patient has decreased. In this case, the treatment regimen indicated in table 950 is to increase the pulmonary vasodilators dosing regimen and decrease the diuretic dosing regimen.

Referring to columns 906, 956, the sensed RAP is greater than the baseline RAP by a threshold. In the event the sensed LAP is higher than the baseline LAP by a threshold, then it is likely the intravascular volume of the patient has increased so the corresponding treatment regimen indicated in table 950 is to increase the diuretic dosing regimen of the patient. As another example and still referring to columns 906, 956, if the sensed LAP is within a threshold of the baseline LAP, then the patient's RHF is likely worsening and the intravascular volume of the patient has increased, or the patient's PVR has increased and the intravascular volume of the patient has increased. In this case, the corresponding dosing regimen indicated in table 950 is to increase pulmonary vasodilators and increase diuretics. As even another example and still referring to columns 906, 956, if the sensed LAP is lower than the baseline LAP by a threshold, then it is likely the patient's RHF is worsening. In this case, the corresponding treatment regimen indicated in table 950 is to increase the pulmonary vasodilators. For any of these dosing regimen changes, the monitoring system 62 may send a notification and/or send corresponding instructions to a therapy device.

In some embodiments, the method 200 (and/or algorithm 99) may incorporate additional metrics such as systemic blood pressure and heart rate to determine the addition of other medications beyond diuretics, vasodilators, and pulmonary vasodilators to address a rise in pressure. For example, an increase in heart rate may determine the need for an increase in dosage of beta blockers instead of vasodilators in order to reduce a high LAP pressure. As another example, a very low blood pressure combined with high LAP and high RAP may determine the need for inotropes instead of diuretics. Additionally, in at least some embodiment, the method 200 (and/or algorithm 99) may be used to indicate the need for treatments beyond medications titrations including lifestyle changes (diet, activity), advanced therapy (VADs, transplant), or therapeutic interventions (intra-atrial shunts, CRTs, ICDs, valve repair/replacement, ablations, etc.)

The disclosed embodiments offer enhanced efficacy and other benefits. For example, no left heart procedure or implant or right atrial or procedure or implant may be needed. Embodiments with the single pressure sensing device can be efficaciously implanted. The methods provide enhanced efficacy. Also, avoiding direct measurements of the atrial septum leaves the atrial septum open or available for procedures such as an atrial shunt, occlusion, left atrial appendage occlusion, mitral valve repair/replacement, mitral chordae repair/replacement and/or afib ablation.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale but may be exaggerated to illustrate various aspects of the present disclosure, and in that regard, the drawing figures should not be construed as limiting.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

In embodiments, methods described herein may be used in connection with disease states that may be treated with medications. Before using methods of the types described herein, it may be advantageous to rule out the presence of disease states or comorbidities that may cause pressure increases such as mitral valve or tricuspid valve regurgitation or atrial fibrillation, that may benefit from other treatment approaches or procedures such as surgery, rather than medication.

What is claimed is:

1. A medical system, comprising:

a sensing device including a pressure sensor for monitoring and providing RVP information representative of right ventricle heart pressures over a period of time, wherein at least the pressure sensor is configured for implantation into a right ventricle of a patient's heart;

one or more processors, wherein the one or more processors are coupled to the sensing device to receive the RVP information sensed by the sensing device, and are configured to receive a patient condition, and wherein the one or more processors are configured to:

determine a right atrial filling pressure based on the RVP information;

determine a left atrial filling pressure based on the RVP information; and produce an indication of a treatment regimen for the patient based upon the patient condition, the right atrial filling pressure, and the left atrial filling pressure;

a memory unit configured to store the right atrial filling pressure, the left atrial filling pressure, and the patient condition; and a display device to display the indicated treatment regimen, right atrial filling pressure and the left atrial filling pressure, wherein the condition is at least one from the group of: left heart failure, right heart failure, and primary pulmonary disorder.

2. The medical system of claim 1 wherein the one or more processors are coupled to receive the RVP information from the sensing device by a wireless communication link.

3. The medical system of claim 1 wherein:

the sensing device comprises a wireless transmitter to wirelessly transmit the RVP information; and the one or more processors are coupled to receive the RVP information wirelessly transmitted by the sensing device.

4. The medical system of claim 1 wherein the sensing device comprises a housing configured for attachment to a wall in the right ventricle of the heart.

5. The medical system of claim 4 wherein the sensing device comprises an anchor for attaching the sensing device to the wall of the right ventricle of the heart.

6. The medical system of claim 1 wherein the sensing device is configured to be entirely located in the right ventricle.

7. The medical system of claim 1 wherein the sensing device comprises:

an antenna to receive electromagnetic energy;

a wireless transmitter; and wherein the sensing device is configured to be energized by the electromagnetic energy received by the antenna, and to transmit the RVP information by the wireless transmitter when energized.

8. The medical system of claim 7 wherein the sensing device is configured to not transmit the RVP information until it is energized.

9. The medical system of claim 1 wherein the one or more processors are configured to determine the right atrial filling pressure using the RVP information as a surrogate for the right atrial filling pressure.

10. The medical system of claim 1 wherein the one or more processors are configured to determining the right atrial filling pressure based on heart pressure information consisting of the RVP information.

11. The medical system of claim 1 wherein the one or more processors are configured to determine the right atrial filling pressure based on the RVP information at end diastole.

12. The medical system of claim 1 wherein the one or more processors are configured to:

receive electrical information representative of electrical activity of the heart;

identify a time of end diastole of the heart based on the electrical information; and determine the right atrial filling pressure based on the RVP information at the identified time of end diastole of the heart.

13. The medical system of claim 1 wherein the one or more processors are configured to determine the left atrial filling pressure using the RVP information as a surrogate for the left atrial filling pressure.

14. The medical system of claim 1 wherein the one or more processors are configured to determine the left atrial filling pressure based on a slope of the RVP information.

15. The medical system of claim 14 wherein the one or more processors are configured to determine the left atrial filling pressure using the right ventricular pressure represented by the RVP information at a time corresponding to a maximum or a peak of the slope of the RVP information as a surrogate for estimated pulmonary artery diastolic pressure, and using the estimated pulmonary artery diastolic pressure as a surrogate for the left atrial filling pressure.

16. The medical system of claim 1 wherein the one or more processors are configured to determine the left atrial filling pressure based on heart pressure information consisting of the RVP information.

17. The medical system of claim 1 wherein the system is configured to determine the right atrial filling pressure without directly monitoring pressure in the right atrium, and to determine the left atrial filling pressure without directly monitoring pressure in the left atrium.

18. The medical system of claim 1 wherein the sensing device is configured to provide the RVP information over one or more cycles of diastole and systole.

19. The medical system of claim 1 wherein the one or more processors are remote from the patient associated with the RVP information.

20. The medical system of claim 1 wherein to determine the treatment regimen of the patient, the one or more processors are configured to:

compare the right atrial filling pressure to a baseline right atrial pressure; and compare the left atrial filling pressure to a baseline left atrial pressure.

21. The medical system of claim 1 wherein to determine the treatment regimen of the patient, the one or more processors are configured to compare the right atrial filling pressure and the left atrial filling pressure.

22. The medical system of claim 1 wherein to determine the treatment regimen for the patient, the one or more processors are configured to provide a notification to increase a dosage of the treatment regimen.

23. The medical system of claim 1 wherein to determine the treatment regimen for the patient, the one or more processors are configured to provide a notification to decrease a dosage of the treatment regimen.

24. The medical system of claim 1 wherein the one or more processors are incorporated into an implantable medical device.

25. The medical system of claim 1 wherein the one or more processors are incorporated into a device located external to the patient.

26. The medical system of claim 1 wherein to determine the treatment regimen of the patient, the one or more processors are configured to provide a notification to increase at least one treatment selected from the following group of treatments: vasodilators, diuretics, pulmonary vasodilators, neurohormonal antagonists, beta blockers, and inotropes.

27. The medical system of claim 1 wherein to determine the treatment regimen of the patient, the one or more processors are configured to provide a notification to decrease at least one treatment selected from the following group of treatments: vasodilators, diuretics pulmonary vasodilators, neurohormonal antagonists, beta blockers, and inotropes.

28. The medical system of claim 1 wherein the sensing device acquires the RVP information at a frequency greater than 100 Hz.

* * * * *